(12) United States Patent
Tarrand et al.

(10) Patent No.: US 10,897,891 B2
(45) Date of Patent: Jan. 26, 2021

(54) COMPOSITIONS AND METHODS FOR PROLONGED CELL STORAGE

(71) Applicant: Board of Regents, The University of Texas System, Austin, TX (US)

(72) Inventors: Jeffrey Tarrand, Houston, TX (US); Borje Andersson, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 316 days.

(21) Appl. No.: 15/565,510

(22) PCT Filed: Apr. 8, 2016

(86) PCT No.: PCT/US2016/026597
§ 371 (c)(1),
(2) Date: Oct. 10, 2017

(87) PCT Pub. No.: WO2016/164693
PCT Pub. Date: Oct. 13, 2016

(65) Prior Publication Data
US 2018/0070581 A1    Mar. 15, 2018

Related U.S. Application Data

(60) Provisional application No. 62/146,039, filed on Apr. 10, 2015.

(51) Int. Cl.
*A01N 1/02* (2006.01)
*A61K 35/51* (2015.01)
*A61K 35/545* (2015.01)
*A61K 35/28* (2015.01)
*A61K 35/19* (2015.01)

(52) U.S. Cl.
CPC ......... *A01N 1/0221* (2013.01); *A01N 1/021* (2013.01); *A61K 35/19* (2013.01); *A61K 35/28* (2013.01); *A61K 35/51* (2013.01); *A61K 35/545* (2013.01)

(58) Field of Classification Search
CPC ...... A01N 1/0221; A01N 1/021; A61K 35/19; A61K 35/28; A61K 35/51; A61K 35/545
See application file for complete search history.

(56) References Cited

U.S. PATENT DOCUMENTS

| | | |
|---|---|---|
| RE32,874 E | 2/1989 | Rock et al. |
| 4,994,367 A | 2/1991 | Bode et al. |
| 5,017,338 A | 5/1991 | Surgenor |
| 5,256,559 A | 10/1993 | Maraganore et al. |
| 5,358,844 A | 10/1994 | Stossel et al. |
| 5,474,891 A | 12/1995 | Murphy |
| 5,569,579 A | 10/1996 | Murphy |
| 5,656,498 A | 8/1997 | Iijima et al. |
| 5,919,614 A | 7/1999 | Livesey et al. |
| 5,958,670 A | 9/1999 | Goodrich, Jr. et al. |
| 6,866,992 B2 | 3/2005 | Lin et al. |
| 7,638,100 B2 | 12/2009 | Dawes |
| 7,919,465 B2 | 4/2011 | Gyongyossy-Issa et al. |
| 7,989,159 B2 | 8/2011 | Gyongyossy-Issa et al. |
| 8,052,667 B2 | 11/2011 | Rosiello et al. |
| 8,067,151 B2 | 11/2011 | Maurer et al. |
| 2004/0185036 A1 | 9/2004 | Stossel et al. |
| 2008/0138791 A1 | 6/2008 | Hoffmeister et al. |
| 2008/0241244 A1 | 10/2008 | Truong-Le |
| 2009/0017438 A1* | 1/2009 | Roy .................. A01N 1/02 435/1.1 |
| 2009/0041737 A1* | 2/2009 | Maurer ............... A01N 1/02 424/93.72 |
| 2009/0155763 A1 | 6/2009 | Rosiello et al. |
| 2009/0191537 A1 | 7/2009 | Mayaudon et al. |
| 2010/0009334 A1 | 1/2010 | Ilyin et al. |
| 2011/0189151 A1 | 8/2011 | Stossel et al. |
| 2012/0107791 A1 | 5/2012 | Rosiello et al. |
| 2012/0128641 A1 | 5/2012 | Austen, Jr. |
| 2013/0059287 A1 | 3/2013 | Rosiello et al. |

FOREIGN PATENT DOCUMENTS

| | | |
|---|---|---|
| EP | 0108588 | 5/1984 |
| WO | WO 1985-002116 | 5/1985 |
| WO | WO 2006-044790 | 4/2006 |
| WO | WO 2011-011055 | 1/2011 |
| WO | WO 2012-027138 | 3/2012 |
| WO | WO 2012-158983 | 11/2012 |

OTHER PUBLICATIONS

Gulick, A.M. et al., Pentaerythritol propoxylate: a new crystallization agent and cryoprotectant induces crystal growth of 2-methylcitrate dehydratase, 2002, Acta Crystallographica, D58, 306-309 (Year: 2002).*
Yuasa, T. et al., Improved extension of platelet storage in a polyolefin container with higher oxygen permeability, 2004, British Journal of Haematology, 126, 153-159 (Year: 2004).*
Mochida, K. et al., Toxicity of Ethylene Glycol, Diethylene Glycol, and Propylene Glycol to Human Cells in Culture, 1987, Bulletin of Environmental Contamination and Toxicology, 38, 151-153 (Year: 1987).*
Lee, Y. et al., Cryopreservation of Mouse Spermatogonial Stem Cells in Dimethylsulfoxide and Polyethylene Glycol, 2013, Biology of Reproduction, 89(5):109, 1-9 (Year: 2013).*
Barkalo and Hartwig, dynamics and cell "The role of actin filament barbed-end exposure in cytoskeletal motility," *Biochem. Soc. Trans.*, 23; 451-456, 1995.
Berendsen et al., "Successful Supercooled Liver Storage for 4 Days," *Nature Med.*, 20(7):790-793, 2014.
Chernoff et al., "The cellular and molecular basis of the platelet storage lesion," *Transfusion*, 32(4): 386-390, 1992.
Devine et al., "The Platelet Storage Lesion," *Clin. Lab. Med.*, 30:475-487, 2010.

(Continued)

*Primary Examiner* — Louise W Humphrey
*Assistant Examiner* — Anjali Ajit Hirani
(74) *Attorney, Agent, or Firm* — Parker Highlander PLLC

(57) ABSTRACT

Provided in some aspects are methods and compositions for preserving platelets or other cells. In some embodiments, a platelet storage media or cell storage media may comprise a low molecular weight polyethylene glycol (e.g. PEG-400) to allow for extended storage and/or refrigeration of the platelets or cells.

20 Claims, 17 Drawing Sheets

(56) References Cited

OTHER PUBLICATIONS

Egidi et al., "Troubleshooting in platelet storage temperature and new perspectives through proteomics," *Blood Transfusion*, 8:(Suppl 3);s73-s8, 2010.
Fujimoto et al., "Production of functional platelets by differentiated embryonic stem (ES) cells in vitro," *Blood*, 102:4044-4051, 2003.
Hogman, "New trends in the preparation and storage of platelets," *Transfusion*, 32(1):3-6, 1992.
Holm, "Storage and quality assessment of platelets," *Vox Sanguinis*, 74:207-216, 1998.
International Preliminary Report on Patentability issued in corresponding PCT Application No. PCT/US2016/26597, dated Oct. 19, 2017.
International Search Report and Written Opinion issued in corresponding PCT Application No. PCT/US2016/26597, dated Jun. 27, 2016.
Kaushansky, "Lineage-specific hematopoietic growth factors," *N. Engl. J. Med.*, 354(19):2034-45, 2006.
Pascual-Lucas et al., "LPS or ethanol triggers clartrin rafts/caveolae-dependent endocytosis of TLR4 in cortical astrocytes," *J Neurochem.*, 129:448-462, 2014.
Sungaran et al., "The role of platelet a-granular proteins in the regulation of thrombopoietin messenger RNA expression in human bone marrow stromal cells," *Blood*, 95:3094-3101, 2000.
Thon et al., "Platelet Storage Lesion: A New Understanding From a Proteomic Perspective," *Transfusion Med. Rev.*; 22(4): 268-279, 2008.
Tomizuka et al., "Hypersensitivity to thromboxane A2 in cholesterol-rich human platelets," *Thromb. Haemost.*, 64(4):594-599, 1990.
Vadhan-Raj et al. "Safety and efficacy of transfusion of autologous cryopreserved platelets derived from recombinant humant hrombopoien to support chemotherapy associated severe thrombpcytopenia: a randomomized cross over study," *Lancet*, 359:21452152, 2002.
van Lier et al., "Role of membrane cholesterol in platelet calcium signalling in response to VWF and collagen under stasis and flow," *Thromb. Haemost.*, 99(6):1068-1078, 2008.
Yip et al., "Primary platelet adhesion receptors," *IUBMB Life*, 57(2):103-108, 2005.

* cited by examiner

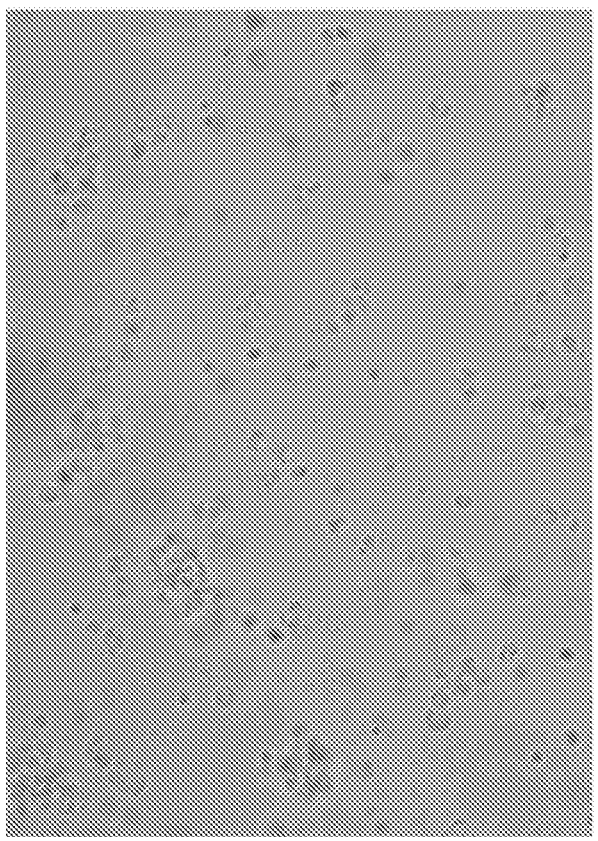 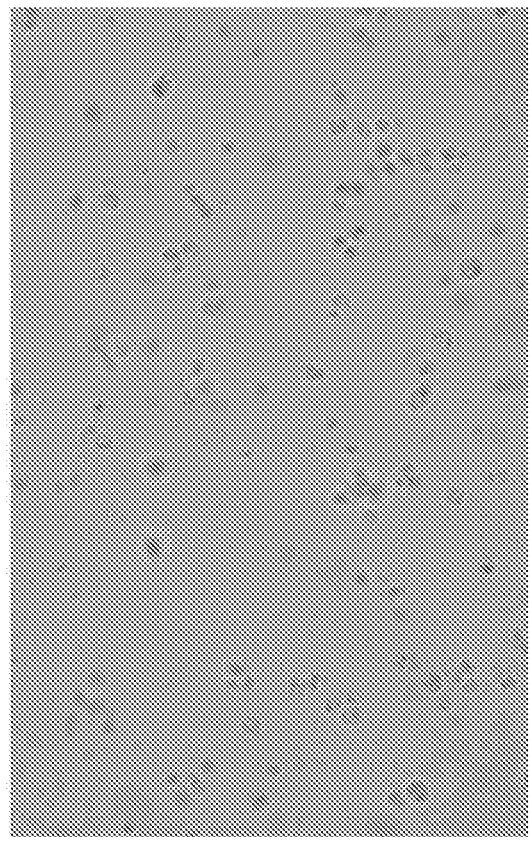
/Control      FIG. 1A      PEG
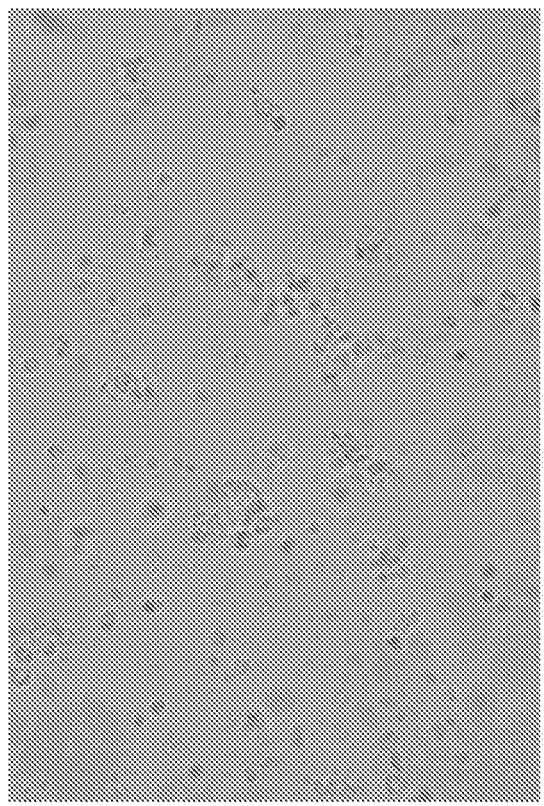 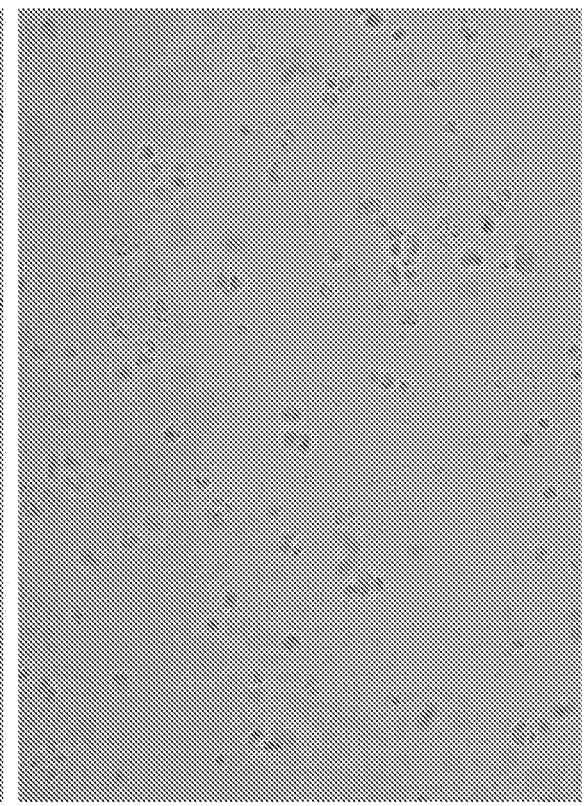
Control      FIG. 1B      PEG Optical density at 690 nm.
Control platelets
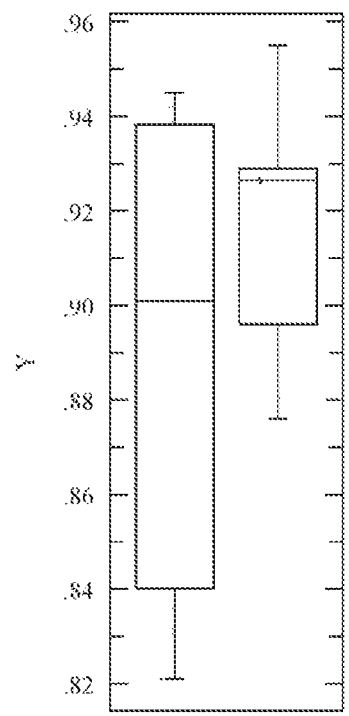
0 control vs. 10 ug/ml
Epinephrine addition
P= 0.18 (NS)
PEG 2% platelets
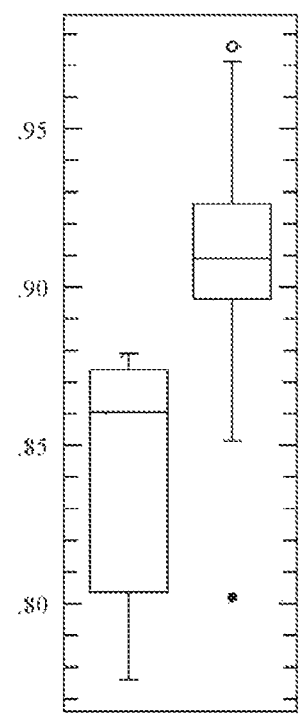
0 control vs. 10 ug/ml
Epinephrine addition
P= 0.019
FIG. 3

Control - 20x photo
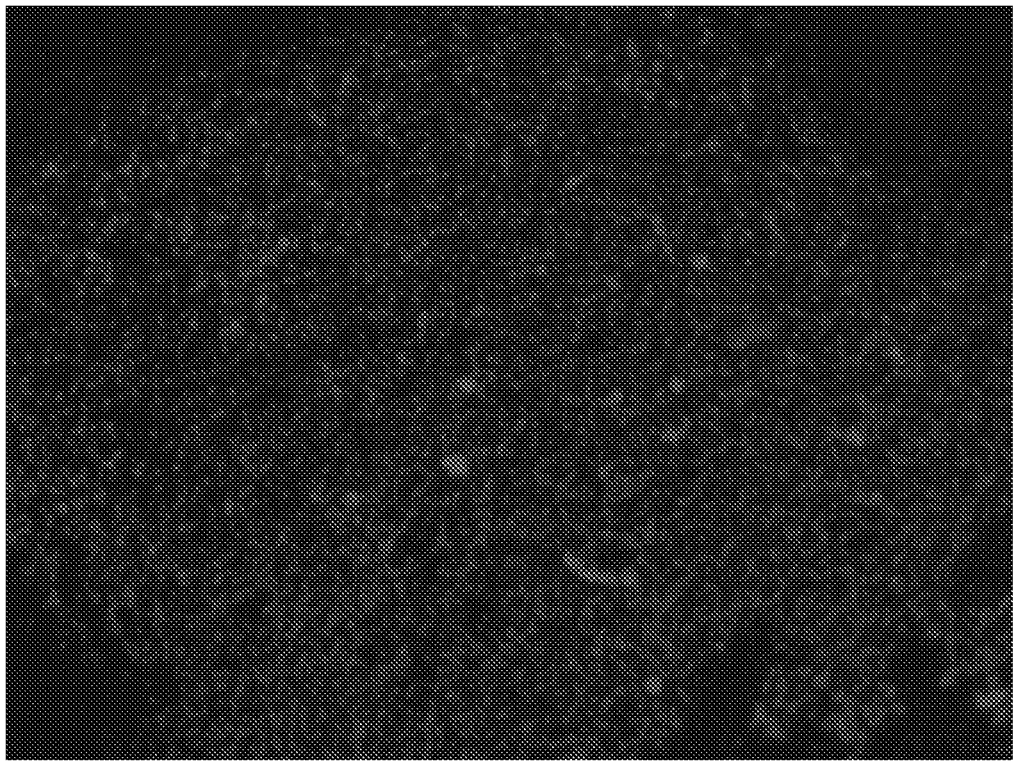
1.5% PEG test solution – 20x photo
FIG. 4

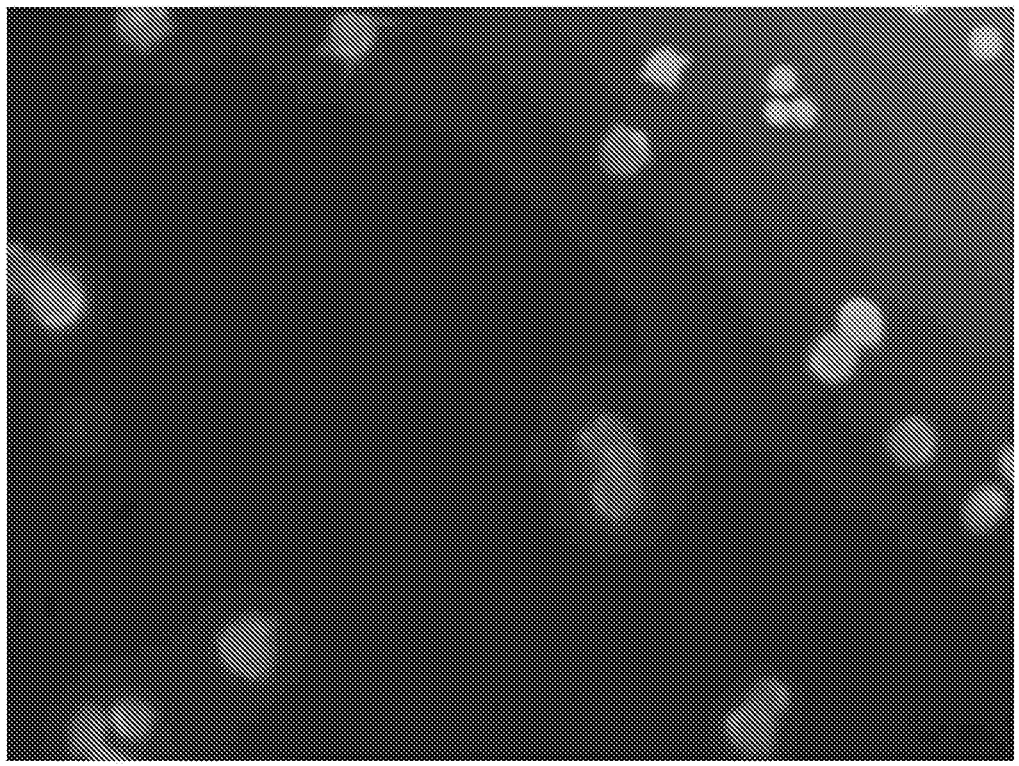
FIG. 5A. Control.
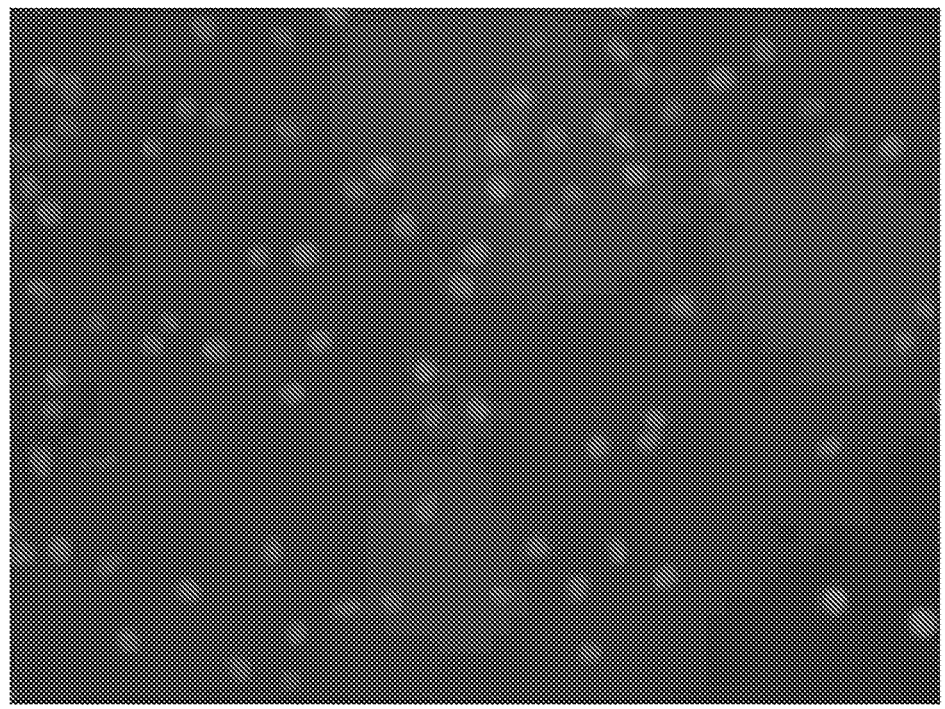
FIG. 5B. PEG test solution.

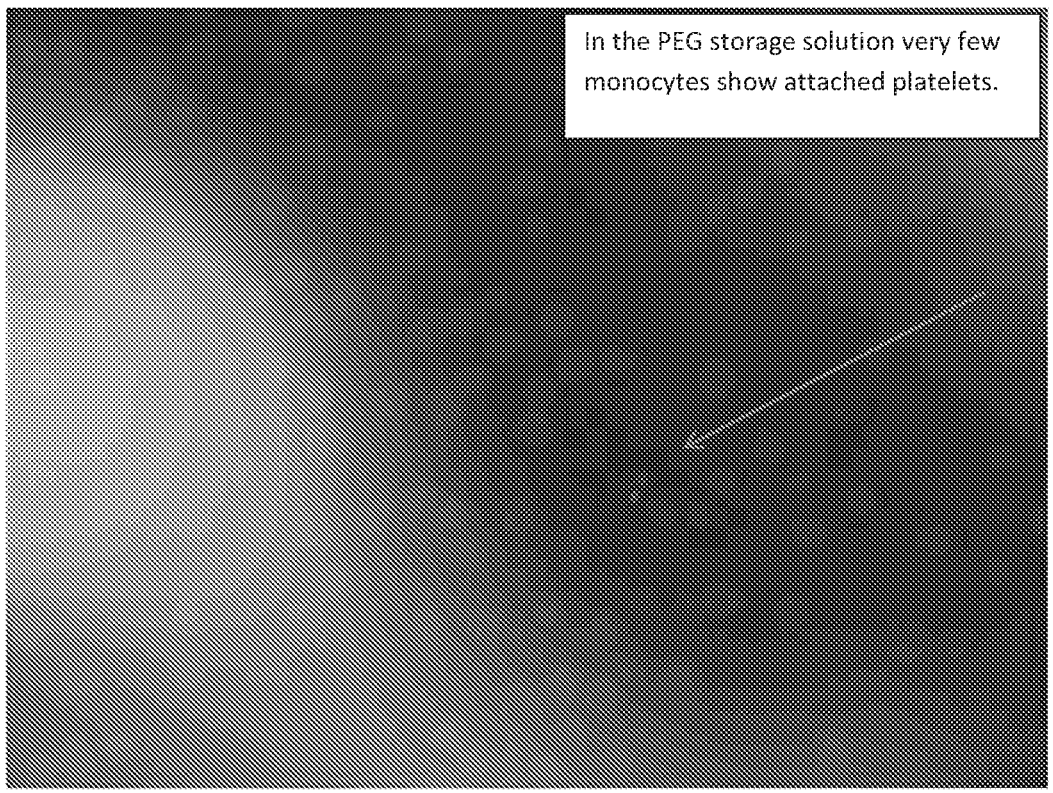
FIG. 5C. PEG test solution.

A= 0 PEG control vs. C= 1% PEG-400 ($P = 0.021$)

Control platelets vs No platelet intervention, $P = 0.0002$

Control platelets vs. 1% PEG-400 ($P = 0.27$, NS)

Control 5°C standard vs. 5°C 2% PEG-400 platelets at 19 days. (P= 0.014)

Graphic (Box plot): 5°C control platelets vs. 5°C, 2% PEG-400 platelets 26 days.

Grams

5°C Control vs. 5°C 2% PEG -400 (P= 0.016)

Platelets with glycerol 6% added.

Matched control - Platelets without glycerol.

COMPOSITIONS AND METHODS FOR PROLONGED CELL STORAGE

This application is a national phase application under 35 U.S.C. § 371 of International Application No. PCT/US2016/026597, filed Apr. 8, 2016, which claims the benefit of U.S. Provisional Patent Application No. 62/146,039, filed Apr. 10, 2015, the entirety of each of which is incorporated herein by reference.

BACKGROUND OF THE INVENTION

1. Field of the Invention

The present invention relates generally to the field of molecular biology and medicine. More particularly, it concerns methods and compositions for prolonged storage of platelets and other cell types.

2. Description of Related Art

Stored or donated blood platelets are very important for a variety of medical interventions including, e.g., management of a variety of bleeding disorders by use of a platelet transfusion procedure. For example, patients receiving chemotherapy require reliable platelets transfusion support to prevent hemorrhagic death.

Platelets normally survive for 4 to 5 days on average in the circulation in vivo, and approximately 150 billion new platelets are produced per day in normal individuals. (Holm S., 1998). Platelet dynamics can be summarized as follows. Adhesion: platelets stick on a foreign surface. Activation: platelets interact with the surface and react to chemical signals. Aggregation: chemical signals result in the release of von Willebrand factor, platelets change shape, and attach or stick to each other to form a clot. Recruitment: activated platelets recruit more platelets and thrombin to the clot. Retraction and wound repair: platelets mediate a physical shrinkage of the clot which further limits bleeding and brings damaged vessel edges in close contact facilitating local remodeling and repair. These properties of platelets are discussed further in Yip et al., 2005.

Unlike essentially all other transplantable tissues, platelets do not tolerate refrigeration and these actively metabolizing cells rapidly lose function at room temperature, and even more quickly at 4° C. (Egidi et al., 2010). Even brief periods of refrigeration can render platelets dysfunctional, resulting in their rapid clearance from the circulation (Egidi et al., 2010). The mechanism underlying the irreversible cold intolerance of platelets is poorly understood. It has been noted that platelets rapidly change shape at refrigeration temperatures. (Tablin et al., 1996; Zucker et al., 1954), It has also been recognized that cholesterol levels can impact platelet function, (Insel et al. 1978), and more recently that cold storage was sufficient to activate the glycoprotein (GP1) platelet receptor (Barkalo and Hartwig, 1995).

The resulting need to keep platelets at room temperature prior to transfusion has imposed a unique set of costly and complex logistical requirements for platelet storage. Because platelets are actively metabolic at room temperature, they require constant agitation in plastic containers permeable to oxygen and that allow release of evolved $CO2$ to prevent the toxic consequences of metabolic acidosis. Prolonged room temperature storage conditions typically result in macromolecular degradation and eventual loss of hemostatic functions of platelets, a set of defects known as "the storage lesion". (Thon el al., 2008, Chernoff et al., 1992). This loss of platelet function is a significant problem in platelet management. Further problems can result from the negative feedback mechanism of platelets on platelet production. Even dysfunctional platelets still possess the active enzyme that metabolizes thrombopoietin, thus stored platelet products may both lack platelet function and still inhibit patient marrow megakaryocytes from producing new platelets. (Sungaran et al., 2000).

Current limitations in the duration for storage of the blood platelets can result in increased blood banking expenses and significant platelet shortages. A large part of the reason for this is that, under current conditions of storage, platelets loose function rapidly. Current regulatory practices typically allow the use of platelets for only up to 5 days following collection. Testing the donated platelets to confirm the absence of bacterial or certain viral contamination problems may require up to a full day. Although there is an urgent medical need for platelets, it is estimated that 300/% must be discarded due to their limited functional 'life span' under current storage conditions. (Devine et al., 2010). Random donor platelets typically must be used within 5 days, and similarly apheresis units expire 24 hr after processing (Hogman et al., 1992). Clearly, there is a need for improved compositions and methods for storing platelets.

SUMMARY OF THE INVENTION

The present invention overcomes limitations in the prior art by providing, in various aspects, improved methods and compositions relating to platelet storage media and methods for promoting prolonged storage and retention of platelet function. The platelet storage media may include a polyethylene glycol (PEG), e.g., about 0.1-5.5% of a lower molecular weight PEG (e.g., about 100-500 g/mol). In some embodiments, it is anticipated that one or more of the following cryoprotectants (e.g., having a molecular weight of about 200-1000, or 200-500 g/mol) may be used in combination with, or may be substituted for, the PEG in the media to promote prolonged platelet storage and/or retention of platelet function: glycerol propoxylate (e.g., $M_n$~266), trimethylolpropane ethoxylate (e.g., $M_n$~450), pentaerythritol propoxylate, (e.g., $M_n$~426), or pentaerythritol ethoxylate, (e.g., $M_n$~270). Also provided are methods and compositions relating to improved platelet storage media. In various embodiments, the stored platelets may be administered to a mammalian subject such as a humans to mediate hemostasis or provide a therapeutic benefit. In some embodiments, the platelet storage media may be used to improve storage of other cell types (e.g., stem cells, apheresis derived hematopoietic cells, sperm cells, hematopoietic stem cells, stem cells from cord blood, pluripotent cells, multipotent cells, embryonic stem cells, induced pluripotent stem cells) under refrigerated (e.g., about −5° C.) or freezing (e.g., −70° C.) conditions.

As shown in the below examples, with standard conditions of rotation/mixing, platelet function was observed to be preserved for 26 days at 5° C. and 13 days under room temperature (about ~22-24° C.) without detectable loss of hemostatic function in the mouse using platelet storage media comprising particular compositions of a lower molecular weight PEG (e.g., PEG-400). These results provide a significant improvement over currently used storage conditions, where platelets are derived from donor blood but must be discarded after 5 days of room temperature storage (Devine et al., 2010). Thus, in contrast to the current thirty percent of platelets that are discarded due to age of the donated platelets, the longer lifespan of platelets preserved with PEG in various embodiments of the present invention may be used to reduce or eliminate the current wastage of donated platelets. The reduced metabolism observed in cells at refrigeration temperatures should improve or facilitate transport of platelet units and assist with logistics of platelet supply. Cold storage (e.g., storage at 0-10° C.) may be able to provide a significant advantage by reducing microbial growth. Currently, a costly and time consuming process is used to monitor all transfused platelets for microbial contamination. It is envisioned that inclusion of a PEG in platelet storage media in combination with cold storage conditions may be used to reduce or eliminate the need for contamination screening. It is also envisioned that improved preserved platelet function that can be achieved using PEG containing storage conditions and methods as described herein may allow for reduced amounts of total platelets to be transfused to a patient in order to achieve a desired therapeutic response or therapeutic platelet increment. In some embodiments, stored platelets may be used to treat thrombocytopenia.

An aspect of the present invention relates to a method for preserving cells, comprising: (a) admixing cells (e.g., platelets) with a cell media comprising a polyethylene glycol having an average molecular weight of from 200 g/mol to less than 1000 g/mol in a concentration of from about 0.1% (wt/v) to less than 5.6% (wt/v); and (b1) wherein if the cells are platelets, then the method comprises storing the cell media comprising the platelets at a temperature of from about 0.1° C. to about 25° C. (e.g., from about 0.1 to about 15° C., from about 20° C. to about 25° C.); (b2) wherein if the cells are stem cells, apheresis derived hematopoietic cells, sperm cells, hematopoietic stem cells, stem cells from cord blood, pluripotent cells, multipotent cells, embryonic stem cells, or induced pluripotent stem cells, then the method comprises storing the cell media comprising the platelets at a temperature of from about −157° C. to about 15° C.; wherein the cells are platelets, stem cells, apheresis derived hematopoietic cells, sperm cells, hematopoietic stem cells, stem cells from cord blood, pluripotent cells, multipotent cells, embryonic stem cells, or induced pluripotent cells. In some embodiments, the method may involve admixing platelets with a cell media comprising a polyethylene glycol having an average molecular weight of from 200 g/mol to less than 1000 g/mol in a concentration of from about 0.1% (wt/v) to less than 5.6% (wt/v), wherein the method comprises storing the cell media comprising the platelets at a temperature of from about 20° C. to about 25° C. In some embodiments, by further including a cryoprotectant (e.g., glycerol (e.g., 3-12%), DMSO (e.g., 0.5-7%), or a poly-(PEG/PPEG) derivative such as pentaerythritol ethoxylate) in the cell media, the cells may be stored at colder temperatures (e.g., about −5° C. to about 0.1° C., or −5, −4, −3, −2, −1, 0, 0.1° C., or any range derivable therein). In some embodiments, the concentration of the polyethylene glycol is from about 1% to about 5%, from about 1.1% to about 2.5%, or 0.1, 1, 1.5, 2, 2.5, 3, 3.5, 4, 4.5, 5, 5.5, or 5.6%, or any range derivable therein. In some embodiments, the cells are platelets, and wherein the method allows for storage of the platelets for more than 5 days without irreversible aggregation of the platelets. In some embodiments, the method allows for storage of the platelets for at least 5-30 days without irreversible aggregation. The temperature may be from about 0.1-10° C., or from about 0.1-5° C. In some embodiments, the cells are stem cells, apheresis derived hematopoietic cells, sperm cells, hematopoietic stem cells, stem cells from cord blood, pluripotent cells, multipotent cells, embryonic stem cells, or induced pluripotent cells; and wherein the temperature is from about −70° C. to about 0° C. In some embodiments, the polyethylene glycol has an average molecular weight of less than 500 g/mol, or less than 420 g/mol. The polyethylene glycol may be PEG-200, PEG-225, PEG-250, PEG-275, PEG-300, PEG-325, PEG-350, PEG-375, PEG-400, PEG-425, PEG-450, PEG-475, or PEG-500. In some embodiments, the polyethylene glycol is PEG-400. In some embodiments, the cell media does not contain or only contains trace amounts of ethyleneglycol, diethylene glycol, and/or triethylene glycol. In some embodiments, the cell media comprises or consists of Acid Citrate Dextrose (ACD) solution, the polyethylene glycol, and the platelets In some embodiments, the media further comprises about 0.3-3% of a compound having the structure:

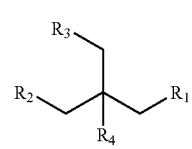

(II)

wherein: $R_1$, $R_2$, and $R_3$ are each independently hydrogen, a polyethylene glycol comprising 1-5 repeating units, or a polypropylene glycol comprising 1-5 repeating units; and $R_4$ is hydrogen, alkyl$_{(C1-12)}$, substituted alkyl$_{(C1-12)}$, or a —(CH$_2$)$_x$—R$_5$; wherein: x is 0, 1, 2, or 3; and $R_5$ is a polyethylene glycol comprising 1-5 repeating units or a polypropylene glycol comprising 1-5 repeating units. In some embodiments, the compound is glycerol propoxylate (e.g., $M_n$~266), trimethylolpropane ethoxylate (e.g., $M_n$~450), pentaerythritol propoxylate, (e.g., $M_n$~426), or pentaerythritol ethoxylate, (e.g., $M_n$~270). In some embodiments, the compound is pentaerythritol propoxylate. The cell media may be comprised in an oxygen permeable polymer or plastic bag or container (e.g., comprising or consisting of an oxygen permeable plastic material such as, e.g., di-(2-ethylhexyl) phthalate (DEHOP)). In some embodiments, if the cells are platelets, then the method comprises storing the cell media comprising the platelets at a temperature of from about 0.1° C. to about 15° C. In some embodiments, the cells are platelets, and wherein the method comprises storing the cell media comprising the platelets at a temperature of from about 20° C. to about 25° C. In some embodiments, the temperature is about −5, −4, −3, −2, −1, 0, 0.1, 1, 2, 3, 4, 5, 6, 7, 8, 9, 10, 11, 12, 13, 14, 15, 16, 17, 18, 19, 20, 21, 22, 23, 24, or 25° C., or any range derivable therein. The method may further comprise storing the cell media under intermittent or constant rotation. In some embodiments, the cell media comprises or consists of Acid Citrate Dextrose (ACD), Citrate Phosphate Dextrose (CPD) or a similar storage buffer solution, the polyethylene glycol, and the platelets. The media may comprise ACD or a platelet additive solution. In some embodiments, the cell media further comprises DMSO or β-cyclodextrin. In some embodiments, the cell media does not comprise DMSO or β-cyclodextrin. The cell media may comprise a phosphate buffered saline (PBS)/ACD mixture, or a PBS/ACD/CPD or other commercial buffer mixture (e.g., as described in Table 1 and/or Table 2). In some embodiments, the cells are platelets. In some embodiments, the cells are stem cells, apheresis derived hematopoietic cells, sperm cells, hematopoietic stem cells, stem cells from cord blood, pluripotent cells, multipotent cells, embryonic stem cells, or induced pluripotent cells. In some embodiments, the media does not contain or only contains trace amounts of ethylene glycol, diethylene glycol, and/or triethylene glycol. In some embodiments, the media may further comprise an additional low molecular weight cryoprotectant such as, e.g., methoxyPEG, glycerol, glycerol propoxylate, trimethylopropane ethoxylate, pentaerythritol ethoxylate, pentaerythritol propoxylate or mixtures of these agents.

Another aspect of the present invention relates to a cell media for preserving platelets, comprising: (a) a polyethylene glycol having an average molecular weight of from 200 g/mol to less than 500 g/mol in a concentration of from about 0.1% to less than 5.6%; (b) ACD, a mixture of phosphate buffered saline (PBS)/ACD, or a mixture of PBS/ACD/CPD or a similar buffer; and (c) viable platelets; wherein the viable platelets (e.g., freshly prepared or isolated) have not undergone irreversible aggregation. In some embodiments, the polyethylene glycol has an average molecular weight of less than 450 g/mol (e.g., less than 420 g/mol). The polyethylene glycol may be PEG-200, PEG-225, PEG-250, PEG-275, PEG-300, PEG-325, PEG-350, PEG-375, PEG-400, PEG-425, PEG-450, PEG-475, or PEG-500. In some embodiments, the media may comprise a polyethylene glycol such as PEG-550, PEG-600, PEG-650, PEG-700, PEG-750, PEG-800, PEG-850, PEG-900, PEG-950, or PEG-1000. In some embodiments, the polyethylene glycol is PEG-400. In some embodiments, the cell media further comprises DMSO or β-cyclodextrin. In some embodiments, the cell media further comprises DMSO, β-cyclodextrin, methoxyPEG, glycerol, glycerol propoxylate, trimethylopropane ethoxylate, pentaerythritol ethoxylate, pentaerythritol propoxylate or a mixtures of one or more of these agents. In some embodiments, the cell media does not comprise DMSO or β-cyclodextrin, or the cell media only contains trace amounts of DMSO or β-cyclodextrin. In some embodiments, the cell media does not comprise an additional cryoprotectant, or the cell media only contains trace amounts of an additional cryoprotectant. In some embodiments, the platelets retain substantially normal hemostatic activity when transplanted in a mammal. The media may further comprises of a compound (e.g., at a concentration of about 0.3-3%) having the structure:

(II)

wherein: $R_1$, $R_2$, and $R_3$ are each independently hydrogen, a polyethylene glycol comprising 1-5 repeating units, or a polypropylene glycol comprising 1-5 repeating units; and $R_4$ is hydrogen, alkyl$_{(C1-12)}$, substituted alkyl$_{(C1-12)}$, or a —(CH$_2$)—R$_5$; wherein: x is 0, 1, 2, or 3; and R$_5$ is a polyethylene glycol comprising 1-5 repeating units or a polypropylene glycol comprising 1-5 repeating units. In some embodiments, the compound is glycerol propoxylate (e.g., $M_n$~266), trimethylolpropane ethoxylate (e.g., $M_n$~450), pentaerythritol propoxylate, (e.g., $M_n$~426), or pentaerythritol ethoxylate, (e.g., $M_n$~270).

Yet another aspect of the present invention relates to a cell media for preserving cells, comprising: (a) a polyethylene glycol having an average molecular weight of from 200 g/mol to less than 500 g/mol in a concentration of from about 0.1% to less than 5.6%; and (c) viable cells, wherein the viable cells are stem cells, apheresis derived hematopoietic cells, sperm cells, hematopoietic stem cells, stem cells from cord blood, pluripotent cells, multipotent cells, embryonic stem cells, or induced pluripotent cells. In some embodiments, the polyethylene glycol has an average molecular weight of less than 420 g/mol. The polyethylene glycol may be PEG-200, PEG-225, PEG-250, PEG-275, PEG-300, PEG-325, PEG-350, PEG-375, PEG-400, PEG-425, PEG-450, PEG-475, or PEG 500. In some embodiments, the polyethylene glycol is PEG-500, PEG-550, PEG-600, PEG-650, PEG-700, PEG-750, PEG-800, PEG-850, PEG-900, PEG-950, or PEG-1000 may be used. In some embodiments, the polyethylene glycol is PEG-400. The media may further comprises of a compound (e.g., at a concentration of about 0.3-3%) having the structure:

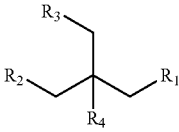

(II)

wherein: $R_1$, $R_2$, and $R_3$ are each independently hydrogen, a polyethylene glycol comprising 1-5 repeating units, or a polypropylene glycol comprising 1-5 repeating units; and $R_4$ is hydrogen, alkyl$_{(C1-12)}$, substituted alkyl$_{(C1-12)}$, or a —(CH$_2$)$_x$—R$_5$; wherein: x is 0, 1, 2, or 3; and $R_5$ is a polyethylene glycol comprising 1-5 repeating units or a polypropylene glycol comprising 1-5 repeating units. In some embodiments, the compound is glycerol propoxylate (e.g., $M_n$~266), trimethylolpropane ethoxylate (e.g., $M_n$~450), pentaerythritol propoxylate, (e.g., $M_n$~426), or pentaerythritol ethoxylate, (e.g., $M_n$~270). In some embodiments, the cell media further comprises DMSO or β-cyclodextrin. In some embodiments, the cell media further comprises DMSO, β-cyclodextrin, methoxyPEG, glycerol, glycerol propoxylate, trimethylopropane ethoxylate, pentaerythritol ethoxylate, pentaerythritol propoxylate, or mixtures of 1, 2, 3, 4, 5, or more of these agents In some embodiments, the cell media does not comprise DMSO or β-cyclodextrin, or only contains trace amounts of DMSO or β-cyclodextrin, or other cryoprotectants.

Another aspect of the present invention relates to a bag comprising a cell media of the present invention. The bag may be further defined as a platelet bag or a platelet collection device (e.g., a supplemental storage media additive bag allowing storage media to be added slowly to the bag or collection device). Blood banks typically use interconnected multiple bag blood collection units sold as a complete assembly that includes a needle, and the storage solution in the primary bag. Storage solutions as described herein may be included in a single (primary) bag, in multiple bags, in a specific bag for platelets, in a small pouch, or in a diverter pouch. For example, in some embodiments, a gradual addition of the a cell media as described herein may be added to a platelet bag over a time period of from about 30 seconds to about 5 minutes.

Yet another aspect of the present invention relates to a method of providing platelets to a mammalian subject comprising administering a therapeutically sufficient amount of a cell media of the present invention. In some embodiments, the subject is a human, and wherein the cell media is further defined as a pharmaceutically acceptable cell media. In some embodiments, the pharmaceutically acceptable cell media is formulated for intravenous administration. In some embodiments, the pharmaceutically acceptable cell media may be formulated for topical or parenteral administration.

Another aspect of the present invention relates to a method for preserving cells, comprising: (a) admixing platelets with a cell media comprising a poly-(PEG/PPEG) derivative having an average molecular weight of from 200 g/mol to less than 1000 g/mol (e.g., in a concentration of from about 0.1% (wt/v) to less than 5.6% (wt/v)), wherein the poly-(PEG/PPEG) derivative has the structure:

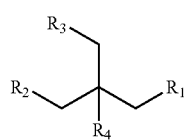

(II)

wherein: $R_1$, $R_2$, and $R_3$ are each independently hydrogen, a polyethylene glycol comprising 1-5 repeating units, or a polypropylene glycol comprising 1-5 repeating units; and $R_4$ is hydrogen, alkyl$_{(C1-12)}$, substituted alkyl$_{(C1-12)}$, or a —(CH$_2$)$_x$—R$_5$; wherein: x is 0, 1, 2, or 3; and $R_5$ is a polyethylene glycol comprising 1-5 repeating units or a polypropylene glycol comprising 1-5 repeating units; and (b1) wherein if the cells are platelets, then the method comprises storing the cell media comprising the platelets at a temperature of from about minus 5° C. to about 25° C.; (b2) wherein if the cells are stem cells, apheresis derived hematopoietic cells, sperm cells, hematopoietic stem cells, stem cells from cord blood, pluripotent cells, multipotent cells, embryonic stem cells, or induced pluripotent cells, then the method comprises storing the cell media comprising the platelets at a temperature of from about −157° C. to about 15° C.; wherein the cells are platelets, stem cells, apheresis derived hematopoietic cells, sperm cells, hematopoietic stem cells, stem cells from cord blood, pluripotent cells, multipotent cells, embryonic stem cells, or induced pluripotent cells. In some embodiments, the poly-(PEG/PPEG) derivative is glycerol propoxylate (M$_n$~266), trimethylolpropane ethoxylate (M$_n$~450), pentaerythritol propoxylate (M$_n$~426), or pentaerythritol ethoxylate, (M$_n$~270). The method may comprise storing the cell media comprising the platelets at a temperature of from about 0.1-15° C. In some embodiments, the temperature is about −5, −4, −3, −2, −1, 0, 0.1, 1, 2, 3, 4, 5, 6, 7, 8, 9, 10, 11, 12, 13, 14, 15, 16, 17, 18, 19, 20, 21, 22, 23, 24, or 25° C., or any range derivable therein. The method may comprise intermittently or continuously rotating the cells. In some embodiments, the concentration of the ply(PEG/PPEG) is from about 1% to about 5%, from about 1.1% to about 2.5%, or 0.1, 1, 1.5, 2, 2.5, 3, 3.5, 4, 4.5, 5, 5.5, or 5.6%, or any range derivable therein.

Yet another aspect of the present invention relates to a cell media for preserving platelets, comprising: (a) a poly-(PEG/PPEG) derivative having an average molecular weight of from 200 g/mol to less than 1000 g/mol (e.g., in a concentration of from about 0.1% to less than 5.6%); wherein the poly-(PEG/PPEG) derivative has the structure:

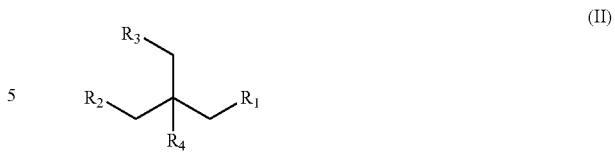

wherein: $R_1$, $R_2$, and $R_3$ are each independently hydrogen, a polyethylene glycol comprising 1-5 repeating units, or a polypropylene glycol comprising 1-5 repeating units; and $R_4$ is hydrogen, alkyl$_{(C1-12)}$, substituted alkyl$_{(C1-12)}$, or a —(CH$_2$)$_x$—R$_5$; wherein: x is 0, 1, 2, or 3; and $R_5$ is a polyethylene glycol comprising 1-5 repeating units or a polypropylene glycol comprising 1-5 repeating units; (b) ACD or a mixture of phosphate buffered saline (PBS)/ACD; and (c) viable platelets; wherein the viable platelets have not undergone irreversible aggregation. In some embodiments, the poly-(PEG/PPEG) derivative is glycerol propoxylate (M$_n$~266), trimethylolpropane ethoxylate (M$_n$~450), pentaerythritol propoxylate (M$_n$~426), or pentaerythritol ethoxylate, (M$_n$~270).

Another aspect of the present invention relates to a cell media for preserving cells, comprising: (a) a poly-(PEG/PPEG) derivative having an average molecular weight of from 200 g/mol to less than 1000 g/mol (e.g., in a concentration of from about 0.1% to less than 5.6%); wherein the poly-(PEG/PPEG) derivative has the structure:

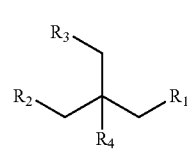

(II)

wherein: $R_1$, $R_2$, and $R_3$ are each independently hydrogen, a polyethylene glycol comprising 1-5 repeating units, or a polypropylene glycol comprising 1-5 repeating units; and $R_4$ is hydrogen, alkyl$_{(C1-12)}$, substituted alkyl$_{(C1-12)}$, or a —(CH$_2$)$_x$—R$_5$; wherein: x is 0, 1, 2, or 3; and $R_5$ is a polyethylene glycol comprising 1-5 repeating units or a polypropylene glycol comprising 1-5 repeating units; and (c) viable cells, wherein the viable cells are stem cells, apheresis derived hematopoietic cells, sperm cells, hematopoietic stem cells, stem cells from cord blood, pluripotent cells, multipotent cells, embryonic stem cells, or induced pluripotent cells. In some embodiments, the poly-(PEG/PPEG) derivative is glycerol propoxylate (M$_n$~266), trimethylolpropane ethoxylate (M$_n$~450), pentaerythritol propoxylatepropoxylate (M$_n$~426), pentaerythritol ethoxylateethoxylate (M$_n$~270), or methoxy-PEG.

Yet another aspect of the present invention relates to a bag comprising the cell media of the present invention or as described above. In some embodiments, the bag is further defined as a platelet bag or a platelet collection device (e.g., an oxygen-permeable bad or collection device).

Another aspect of the present invention relates to a method of providing platelets to a mammalian subject (e.g., a human) comprising administering a therapeutically sufficient amount of a cell media of the present invention or as described above.

Yet another aspect of the present invention relates to a method for preserving cells, comprising: (a) admixing platelets with a cell media comprising: (i) a polyethylene glycol having an average molecular weight of from 200 g/mol to less than 1000 g/mol in a concentration of from about 0.1% (wt/v) to less than 5.6% (wt/v); and (ii) a cryoprotectant; (b) wherein the method comprises storing the cell media comprising the platelets at a temperature of from about −0.5° C. to about 0° C.; wherein the cells are platelets, stem cells, apheresis derived hematopoietic cells, sperm cells, hematopoietic stem cells, stem cells from cord blood, pluripotent cells, multipotent cells, embryonic stem cells, or induced pluripotent. In some embodiments, the cryoprotectant is glycerol, DMSO, or a poly-(PEG/PPEG) derivative. In some embodiments, the cryoprotectant is glycerol. The cell media may comprise about 3-12% glycerol. The cryoprotectant may be DMSO. The cell media may comprise about 0.5-7% DMSO. In some embodiments, the cryoprotectant is the poly-(PEG/PPEG) derivative, wherein the poly-(PEG/PPEG) derivative is pentaerythritol ethoxylate. The cell media may comprise about 0.3-3% pentaerythritol ethoxylate.

In some embodiments, the platelet storage solution may comprise 1, 2, 3, 4, 5, 6, 7, 8, or more component(s) included in a platelet additive solution as described in Table 1 or Table 2 below. In some embodiments, a platelet storage solution comprises all of the components in one of the platelet additive solution shown in Table 1 or Table 2.

TABLE 1

Approximate formulation of Platelet Additive Solutions (mM)

| Chemical | PAS-1p | PAS-II (T-sol) | PAS-III (intersol) | PAS111M ssp | PAS G | Msol |
|---|---|---|---|---|---|---|
| NaCl | 90 | 116 | 77 | 69 | 90 | 110 |
| NaAcetate | 27 | 30 | 30 | 30 | 27 | 15 |
| NaCitrate | — | 10 | 10 | 10 | 11 | 10 |
| KCl | 5 | — | — | 5 | 5 | 5 |
| MgCl$_2$ | 3 | — | — | 1.5 | 1.5 | 3 |
| Posphate | — | — | 26 | 26 | — | 4 |
| NaGluconate | 23 | — | — | — | 23 | — |
| Glucose | — | — | — | — | — | 30 |
| NaHCO$_3$ | — | — | — | — | — | 12 |

TABLE 2

Platelet Additive Solutions - Anticoagulant-Preservative Solutions*
Anticoagulant-Preservative (g/L)

| | Trisodium Citrate | Citric Acid | NaPO4 | Dextrose | Adenine | Shelf Life |
|---|---|---|---|---|---|---|
| Anticoagulant citrate-dextrose A (ACD-A)† | 22.0 | 8.0 | 0 | 24.5 | 0 | 21 days |
| Citrate-phosphate dextrose (CPD) | 26.3 | 3.27 | 2.22 | 25.5 | 0 | 21 days |
| Citrate-phosphate-dextrose-dextrose (CP2D) | 26.3 | 3.27 | 2.22 | 51.1 | 0 | 21 days |
| Citrate-phosphate-dextrose-adenine (CPDA-1) | 26.3 | 3.27 | 2.22 | 31.9 | 0.275 | 35 days |

*63 mL/450 mL collection, 70 mL/500 mL collection
†ACD is used for apheresis components.

As used herein, a "platelet storage media" refers to a media as described herein that can be used to store platelets or other cell types under refrigerated or freezing conditions. For example, in some embodiments, the platelet storage media may be used to store platelets under refrigerated or freezing conditions. In some embodiments, the platelet storage media may be used to store other cell types such as, e.g., stem cells, apheresis derived hematopoietic cells, sperm cells (e.g., bovine sperm cells), hematopoietic stem cells, stem cells from cord blood, pluripotent cells, multipotent cells, embryonic stem cells, or induced pluripotent cells. In some embodiments the other cells are stored in a platelet storage media without the presence of platelets in the storage media. In some preferred embodiments, the platelet storage media comprises a PEG (e.g., about 1-3% PEG-400).

The stored platelets may be administered to a mammalian subject (e.g., a human patient) to treat a variety of diseases. For example, stored platelets may be administered to a patient to treat, e.g., thrombocytopenia, or platelets may be as a source of platelet derived growth factor to assist wound repair. In some embodiments, platelets or hematopoietic stem cells may be stored in a platelet storage media as described herein at freezing temperatures (e.g., from about 0 to about −70° C.), and these approaches may be useful for the collection and/or storage of apheresis derived hematopoietic stem cells.

The term "pharmaceutically acceptable" means a non-toxic material that does not interfere with the effectiveness of the biological activity of the platelets and that is a non-toxic material that is compatible with a biological system such as a cell, cell culture, tissue, or organism. Pharmaceutically acceptable carriers include diluents, fillers, salts, buffers, stabilizers, solubilizers, and other materials which are well known in the art, for example, a buffer that stabilizes the platelet preparation to between a pH of from about 6.5 (e.g., Acid Citrate Dextrose) to about 7.4 or about 7.4, the physiological pH of blood, is an example of a pharmaceutically acceptable composition suitable for use with the present invention. In some embodiments, the pharmaceutically acceptable composition is contained in an oxygen permeable plastic bag material (e.g., di-(2-ethylhexyl) phthalate (DEHOP)).

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Results showing control platelets at 5° C. for 26 days as compared to platelets stored with the addition of PEG-400 at 2% final concentration at 5° C. for 26 days. Control results are shown on the left side, and platelets stored with PEG-400 are shown on the right side of FIG. 1A and FIG. 1B.

FIG. 2A, PBS (Control) plus 10% hydrogen peroxide showing extensive aggregation. FIG. 2B, PBS-2%-PEG400 (Test) plus 10% hydrogen peroxide—showing less aggregation than PBS 10% $H_2O_2$ control.

FIG. 3: Responsiveness of control (PBS storage) and test (2% PEG-400 storage) platelets to 0 or 10 μg epinephrine challenge.

FIGS. 4A-B: FIG. 4A, degranulation of von Willebrand factor (vWF) was observed in the control chilled platelets. FIG. 4B, Inclusion of 1.5% PEG-400 in storage media prevented vWG degranulation at 5° C.

FIGS. 5A-B: FIG. 5A, Control: strongly fluorescent platelets attached to the larger U937 cell. FIG. 5B and FIG. 5C, PEG test solution: U937 membranes were observed to be smooth and showed only a few attached strongly fluorescent platelets.

FIG. 6A, C=PBS control image. Control PBS platelets showed cholesterol capping. FIG. 6B, P2=PBS+2%-PEG400 image. Test platelets stored in 2% PEG-400 overnight showed less cholesterol capping. FIG. 6C, P4=PBS plus 4% PEG-400. Test platelets stored in 4% PEG-400 overnight showed less cholesterol capping.

DESCRIPTION OF ILLUSTRATIVE EMBODIMENTS

Figure 2A:
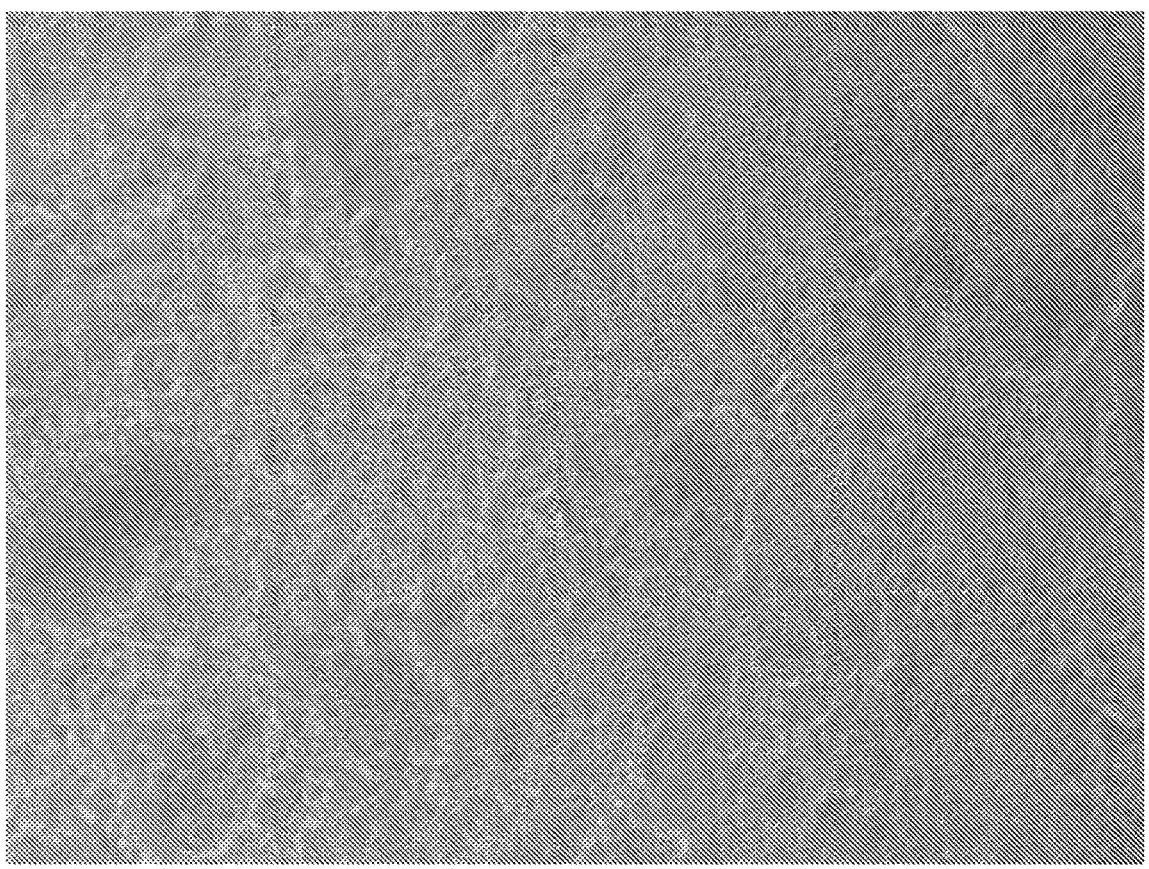
FIGS. 2A-B.

The present invention, in various aspects, provides methods and compositions for preserving platelet function after collection. For example and as shown in the below examples, it has been found that relatively low concentrations of lower molecular weight PEG may be included in a platelet storage media to allow for extended storage of the platelets. In contrast to these findings, it was found that inclusion of either (1) higher molecular weight PEG in a platelet storage media, or (2) inclusion of higher concentrations of a PEG in a platelet storage media were not able to replicate the beneficial effects of including a lower concentration of a lower molecular weight PEG in the platelet storage media, and irreversible aggregation of platelets was observed, rendering the platelets unsuited for therapeutic administration. Without wishing to be bound by any theory, these results are consistent with the idea that lower molecular weight PEG may interact with platelet membranes and inhibit irreversible aggregation of platelets during storage.

I. Platelet Storage Compositions and Methods

Platelets are small anucleate cells that are needed for normal coagulation function. Platelets, also called thrombocytes, are produced by megakaryocytes in the bone marrow. Platelets are generally about 2-3 um diameter and are membrane bound, anucleate cells found in the bloodstream. They help protect injured mammals from hemorrhagic blood loss by adhering to sites of blood vessel injury and by the formation of a platelet-fibrin clot. Patients with low numbers of platelets in the bloodstream may hemorrhage spontaneously, typically bleeding into the gut, lungs, or brain. These events can be life threatening.

Platelets may be purified from donor blood via several approaches. For example, platelet concentrates (PCs) may be made from individually donated whole blood units, and pools of several donors (e.g., 5 to 6 "random" donors) may be transfused to provide a useful increment or improvement of platelet support or function for a patient. Alternatively, platelets may be collected from donors using an apheresis procedure. The apheresis procedure typically involves aseptic separation of platelets, where the non-platelet blood cells and plasma are returned to the donor. The donated platelets may be tested to confirm the absence of bacterial or certain viral contamination problems. Regardless of the initial method of preparation, the storage time is normally limited; however, improvements in the storage of platelets can be achieved in various embodiments using the platelet storage compositions and methods, as described herein.

In some instances, platelets may be stored in a storage media, e.g., under constant agitation on a flat-bed rotator (e.g., about 20-90, 20, 30, 40, 50, 60, or 70 cycles per minute, or any range derivable therein, or 20-200 cycles per minute; using, e.g., with a 1 inch stroke radius), at about 20-24° C. (68-75.2° F.) or about 20-25° C., in oxygen permeable plastic bags composed of di-(2-ethylhexyl) phthalate (DEHOP). In some embodiments, platelets may be refrigerated, e.g., at about 1-15° C., or 1, 2, 3, 4, 5, 6, 7, 8, 9, 10, 11, 12, 13, 14, 15 degrees C., or any range derivable therein. In some embodiments, constant agitation may be useful for extending storage of platelets; nonetheless, it is anticipated that repeated or occasional agitation or no agitation may be used in some embodiments for the storage of platelets as described herein.

In some embodiments, recombinant thrombopoietin may be administered to a patient in combination with platelets stored using methods of compositions as described herein. Thrombopoietin is a glycoprotein hormone produced by the liver and kidney which can regulates the production of platelets (Kaushansky 2006).

In some embodiments, human stem cells may be differentiated into platelet producers in vitro and stored using compositions and methods as described herein. For example, platelets may be produced from human stem cells using the methods as described in Fujimoto et al., 2003 (Fujimoto et al., 2003).

Additional methods for the production or storage of platelets that may be used in combination with aspects of the present invention include, e.g., those described in U.S. 2012/0107791 or U.S. Pat. No. 8,052,667, which are incorporated by reference in their entirety without disclaimer. For example, in some embodiments, N-acetylneuraminic acid (sialic acid), or certain nucleotide-sugar molecules, such as CMP-sialic acid or UDP-galactose may optionally be included in a platelet storage media.

In some embodiments, the platelet storage media may optionally contain one or more of citrate, acetate, calcium, L-carnitine, oxaloacetate, and/or aspartate, e.g., as described in US 20090191537. In some embodiments, the platelet storage media may optionally contain one or more of buffered Ringers-citrate solution, low glucose, glutamine and or oxaloacetate, malate, fumarate, oxalosuccinate, isocitrate, cis-aconitate, e.g., as described in WO1985002116. In some embodiments, a calcium chelator with an actin inhibitor may be included in a platelet storage media (e.g., as described in U.S. Pat. No. 5,358,844).

In some embodiments, platelets are stored in the storage media under room temperature or refrigerated (e.g., 1-10° C., or about 5° C.) and then directly administered or warmed to room temperature prior to administration to a subject. Thus, in some embodiments, the platelet storage media is a pharmacologically acceptable solution or composition that does not require the removal of components from the platelet storage media or further removal or purification of platelets from the platelet storage media. The ability to directly administer platelets in a storage media (e.g., comprising a low molecular weight PEG such as a pharmaceutically acceptable low molecular weight PEG exhibiting little or no toxicity) can allow, e.g., efficient application or administration of platelets with minimal modification of typical blood banking practices.

In some embodiments, the platelet storage media comprises saline, phosphate buffered saline (PBS), or Anticoagulant Citrate Dextrose as a base solution (e.g., ACD, ACD-A, CPD, or similar platelet additive solution) in combination with a low molecular weight PEG. For example, the low molecular weight PEG may be PEG-400 in ACD-A.

Additional components that may be included in a platelet storage media as described herein include DMSO. The DMSO may be present at a concentration of about 0.1 to 5%, 1-3%, 0.1-3° %, 1-5%, or 0.1, 0.5, 1, 1.5, 2, 2.5, 3, 3.5, 4, 4.5, 5%, or any range derivable therein.

In some embodiments, the platelet storage media may contain cholesterol. For example, cholesterol may be added to a platelet storage media to achieve a level of about 100-200 mg/dL range (e.g., in a platelet storage bag or unit of platelets). The amount of cholesterol may range, e.g., from about 25, 50, 75, 100, 125, 150, 175, 200, 225, or 250 mg/dL, or any range derivable therein. In some embodiments, the platelet storage media may contain low cholesterol or diluted plasma or one or more agents that can adsorb cholesterol. In some embodiments, the platelet storage media may provide a low cholesterol, low glucose containing modified ACD buffer with the addition of about 0.5-3% of a low molecular weight PEG.

In some embodiments, the platelet storage media may comprise or consist of a sterile Polyethylene glycol (e.g., PEG-400 or a molecular weight 400 PEG) in Adenosine, Citrate Dextrose solution. For example if a final concentration of 2% PEG-400 is desired then the standard 10×ACD solution [Trisodium Citrate 22.0 g/L, Citric Acid 8.0 g/L, Dextrose 24.5 g/L] can be formulated to contain 20% PEG-400. When 9 volumes of fresh platelet/plasma concentrate is added to this 1 volume in the platelet bag, the result will be 2% PEG 400 in 1× standard ACD solution. In some embodiments, the PEG ACD solution is added slowly to the platelets following plasma reduction. In other embodiments, the molecular weight and percent PEG in the composition can vary within a range. In some embodiments, DMSO (e.g., about 1-7% DMSO) can be included to facilitate cell freezing.

A. Polyethylene Glycol (PEG)

PEG is the polymeric form of ethylene glycol. PEG has the formula:

$$H(OCH_2CH_2)_nOH \qquad (I)$$

wherein the repeating unit, n, is an integer. In some aspects, the nomenclature used to describe PEG includes the average molecular weight of the polymer (e.g. PEG-400; PEG-500, PEG-600, etc.). As would be obvious to a person of skill in the art, the average molecular weight does not mean that any particular PEG molecule within the composition has the noted molecular weight but rather that the composition as a whole has the average molecular weight corresponding to that value. In some embodiments, the PEG molecule can have one or both of the terminal hydrogen atom can be replaced with another group including but not limited to an alkyl group (e.g. a methyl group or an ethyl group), or a reactive moiety used to attach the PEG to another compound. For example, a PEG-400 composition generally comprises PEG molecules with 8 and 9 repeating units as shown in the formula above, but may also comprises individual PEG molecules with less than 8 or more than 9 repeating units. As the value in the name of the PEG composition represents the average molecular weight, the overall polymer average molecular weight may be modified to obtain an average molecular weight from less than 200 to over a 1000 g/mol (e.g. from 2 repeating units to about 22 repeating units, more preferably from 4 repeating units to about 22 repeating units). In some aspects, the PEG is selected with an average molecular weight of about 200, 225, 250, 275, 300, 325, 350, 375, 400, 425, 450, 475, 500, 525, 550, 575, or 600 g/mol, or any range derivable therein. In some embodiments, the PEG has an average molecular weight equal to or less than PEG-1000 (e.g., PEG-400). In some embodiments, a platelet storage media contains or comprises about 1-3% of PEG-400, about 1-3% PEG-300, about 1-3% PEG-350, about 1-3% PEG-500, or about 1-3% PEGs consisting of a mixture of PEG molecules having a molecular weight (mwt) between 300 and 500. In some embodiments, the concentration of the polyethylene glycol is from about 1% to about 5%, from about 1.1% to about 2.5%, or 0.1, 1, 1.5, 2, 2.5, 3, 3.5, 4, 4.5, 5, 5.5, or 5.6%, or any range derivable therein.

In some embodiments, a methoxy-PEG or Poly-(methoxy-PEG/PEG) derivative may have the advantage of increased stability. Further, one or more poly-(PEG/PEG) or poly-(PEG/PPG) derivatives (e.g., having a molecular weight of from about 200-700, or 200-600 g/mol) may be used to promote survival of platelets in storage, e.g., during refrigerated or freezing conditions. The poly-(PEG/PPG) derivative preferably has the structure:

(II)

wherein:

R$_1$, R$_2$, and R$_3$ are each independently hydrogen, a polyethylene glycol comprising 1-5 repeating units, or a polypropylene glycol comprising 1-5 repeating units; and R$_4$ is hydrogen, alkyl$_{(C1-12)}$, substituted alkyl$_{(C1-12)}$, or a —(CH$_2$)$_x$—R$_5$; wherein:

x is 0, 1, 2, or 3; and

R$_5$ is a polyethylene glycol comprising 1-5 repeating units or a polypropylene glycol comprising 1-5 repeating units;

For example, it is anticipated that one or more of the following compounds (e.g., having a molecular weight of M$_n$ of about 100-700, or about 200-600 g/mol) could be used in combination with, or substituted for, the PEG in the media to promote prolonged platelet storage and/or retention of platelet function: glycerol propoxylate (e.g., M$_n$~266), trimethylolpropane ethoxylate (e.g., M$_n$~450), pentaerythritol propoxylate, (e.g., M$_n$~426), or pentaerythritol ethoxylate, (e.g., M$_n$~270). In some embodiments, the concentration of the poly(PEG/PPEG) is from about 1% to about 5%, from about 1.1% to about 2.5%, or 0.1, 1, 1.5, 2, 2.5, 3, 3.5, 4, 4.5, 5, 5.5, or 5.6%, or any range derivable therein.

As used herein, the phrase "low molecular weight PEG" or "lower molecular weight PEG" are used interchangeably and refer to a PEG having an average molecular weight of from about 200 to about 1000 g/mol, more preferably from about 200 to about 600 g/mol, or from about 300 to about 500 g/mol. In some embodiments, the low molecular weight PEG may have from 2-22, 3-20, 4-15, 4-12, 5-11, 6-10, 7, 8, or 9 repeating units. In some embodiments, the low molecular weight PEG may have 2, 3, 4, 5, 6, 7, 8, 9, 10, 11, 12, 13, 14, 15, 16, 17, 18, 19, 20, 21, or 22 repeating units, or any range derivable therein.

Effective amounts of a PEG (e.g., PEG-400) may range from about 0.1% to about 7% of the platelet storage medium, and more preferably about 1% to 3% of PEG may be included in the platelet storage medium. Effective molecular weights of PEG that may be included in a platelet storage medium may range from 150 to 1000 molecular weight, more preferably 300 to 500 molecular weight, average molecular weight, or nominal molecular weight. The storage conditions may further include one or more of: ACD or similar basal anticoagulant solution, constant agitation, maintenance at room temperature or refrigerated conditions, and/or di-(2-ethylhexyl) phthalate plastic bag, in combination with a storage media containing a lower molecular weight PEG (e.g., PEG-400). PEG-400 is a well-known and generally nontoxic molecule, and it may elute out of platelets to give a blood level ~0.025% per unit transfused. In some embodiments, the lower molecular weight PEG may be cleared by the kidneys of subjects after administration of platelets in a platelet storage media comprising the lower molecular weight PEG.

In some embodiments, inclusion of PEG in platelet storage compositions may result in little or no detectable toxicity when the platelets and storage media are administered to a patient after storage. PEG has been used as a GRAS agent in the food industry, and it has been included in some injectable drug compositions. PEG-400 appears to have relatively low toxicity, and a toxic endpoint ~8 g/Kg or 0.8% for the whole animal was suggested by studies involving dogs (Li et al., 2011), and similar levels are tolerated by primates (e.g., 0.4% of body weight for 11 weeks). (Lockard, 1979). It is anticipated that relatively low levels of PEG that might result in a patient after giving a unit of platelets where PEG is included in the storage media (e.g., 0.025% immediately after transfusion) may be well tolerated and result in little or no toxicity in the patient. Without wishing to be bound by any theory, inclusion of a lower molecular weight PEG in a platelet storage media as described herein may promote stabilization of membrane structure of platelets and/or inhibit cold induced aggregation of cholesterol-raft associated transmembrane complexes. Without wishing to be bound by any theory, the data obtained is consistent with the idea that, in contrast to larger molecular weight PEG, lower molecular weight PEG may be able to penetrate into the membranes of platelets to alter membrane or cell function which may, e.g., prevent or slow the gradual activation that is observed with prolonged room temperature storage and/or prevent or slow the abrupt activation observed under refrigeration conditions.

B. Refrigeration of Platelets in a Platelet Storage Media

In some embodiments, platelets stored in a platelet storage media (e.g., comprising about 1-5% of a lower molecular weight PEG) may be refrigerated. Refrigeration may comprise maintaining platelets at a temperature of about 0.1-15, 0.1-10, 0.1-8, 1-5, 3-6, 4-5, 1, 2, 3, 4, 5, 6, 7, 8, 9, 10, 11, 12, 13, 14, 15, 16, 17, 18, 19, 20, 21, 22, 23, 24, 25 degrees C., or any range therein. In some preferred embodiments, platelets in a platelet storage media may be maintained at about 1-15, 2-7, 3-6, or 5° C. In some embodiments, rotation or movement of the platelets may be carried out, e.g., by maintaining the platelets in the platelet storage media in a platelet bag on a rotator. In some embodiments, the movement or rotation of the platelets is substantially continuous. Nonetheless, it is anticipated that sporadic movement or rotation of platelets may be used in some embodiments, and in some embodiments platelets may be maintained in a platelet storage media for a period of time (e.g., during transport of the platelets) without precluding the clinical and therapeutic use of the platelets.

Refrigeration of platelets is different as compared to freezing platelets below freezing temperatures (e.g., below 0° C.). In some embodiments, it may be possible to maintain the platelets in a platelet storage media as described herein at a temperature near or below 0° C. (e.g., preferably without freezing) for some period of time without precluding clinical use of the platelets, e.g., by including a PEG in the cell storage media as described herein alone or, optionally, in combination with one or more cryoprotectants (e.g., glycerol). Nonetheless, in some preferred embodiments, the platelets are maintained at room temperature or refrigerated conditions, as mentioned above.

As noted in the below examples, PEG containing storage compositions resulted in significantly improved platelet functional survival at 11-14 days under room temperature storage conditions on a flat-bed rotator. Further, platelet functionality was successfully preserved under 5° C. storage conditions with rotation over 26 days. Data with animal studies indicate that it may be possible to maintain platelets under 5° C. storage without the use of continuous rotation. Not requiring rotation may facilitate the transport of platelets between treatment facilities. Without wishing to be bound by any theory, the data obtained supports the idea that inclusion of particular amounts of a lower molecular weight PEG (e.g., from about 1-5% PEG) may inhibit premature activation in current storage conditions. These platelet storage media can allow for storage of platelets at 5° C., and maintaining the platelets under these refrigerated conditions can lower the metabolism of the platelets and facilitate transport of the platelets over a longer period of time. Storage of platelets under refrigerated conditions (e.g., about 1-10° C. or about 5° C.) may also inhibit bacterial contamination, which has been a problem with donated platelets (Yomtovian el al., 1993). It is envisioned that 5° C. storage may, in some embodiments, reduce or obviate the need for bacterial contamination screening. In some embodiments, the combination of one or more of these improvements may significantly reduce the complex logistics currently needed for platelet storage and handling.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

ceutical NDC 0409-4921-34-44-048-DK) was diluted with PBS and 100 ul was added to test wells to give a finial concentration of 10 mcg/ml. The plate was rotated overnight to allow aggregation. The extent of aggregation was read using an ELISA plate reader (Molecular Devises, Vmax) at 690 nm wavelength. Platelets, with and without PEG, were also aggregated by the addition of 10% $H_2O_2$. Hydrogen peroxide is not an agonist for the platelet receptor; however exposure to hydrogen peroxide mimics the platelet storage lesion though membrane ageing. In this study, the inventors tested 2 day old residual platelets form one donor unit by splitting the material in to a 24 well cluster plate. Control platelets had 10% PBS added and were compared to test compositions with the addition of 10% volume PBS plus 2% PEG-400. 10% v/v (Hydrogen peroxide 3%) was then added to all wells simultaneously using a multichannel pipette. Wells were photographed following 1 hr room temperature incubation (see FIGS. 2A-B and FIG. 3). Table 3 presents additional cryoprotective agents scored for the effect on microscopic degranulation (20× high contrast lighting as above).

| Agent* | Mwt | Days at 5° C. | 6% | 3% | 1.5% | 0.75% | 0.38% | Control^ |
|---|---|---|---|---|---|---|---|---|
| Glycerol propoxylate | 266 | 6 | NT | none | fair | fair | none | none |
| Trimethylopropane ethoxylate | 450 | 6 | NT | none | none | none | none | none |
| Pentaerythritol ethoxylate | 270 | 6 | NT | none | none | none | none | none |
| Pentaerythritol Propoxylate | 426 | 6 | NT | none | none | none | fair | none |
| Methoxy PEG | 350 | 6 | NT | good | good | none | none | none |
| Glycerol | 92 | 10 | good | fair | NT | NT | NT | none |

*Final concentrations of cryoprotectants are shown as % solution in ACD-Platelet mixture.
NT, Not tested.
, Results - None = no effect detected ~90% complete degranulation, Fair = 25 to 50% of platelets are non-degranulated. Good = >80 are non-degranulated.
^Controls were made in the same manner as test solutions by mixing ACD PBS containing zero cryoprotectant with test platelets in a 1:1 addition. After 10 min rotation at room temp all samples were transferred to 5° C. and rotated together.

Example 1

Materials and Methods

Platelet Source.

Platelet samples were from the Transfusion Medication service at MDACC. All samples were de-identified residual or discarded donor material less than 3 days old.

Microscopy.

Photomicrographs were taken with a Nikon E400 microscope with an Insight 18.2 Color Camera and Spot 5.1 image capture software. No image adjustments were performed. Fluorescent microscopy was performed using a Leica DMIL photomicroscope and Leica LAS V3.8 image acquisition software. No post photographic image adjustments were made.

Platelet aggregation using epinephrine. Ten ml of 24 hr old platelet residual was derived from one platelet unit and split into two 5 ml aliquots in 50 ml tubes. One sample received 10% phosphate buffered saline (PBS) and one 10% PBS containing PEG400 such that the final PEG concentration was 2%. These samples were placed on a flat-bed rotator with a 1 inch stroke, at 70 cycles per min, at 5° C. for 7 days. 100 ul of these platelet suspensions were added to wells of a 96 well U bottom plate. Epinephrine 0.1 mg/ml (Pharma- Studies of Platelet Degranulation Using Anti-Von Willebrand Factor Immunoflorescent Staining.

Functional, non-degranulated, platelets should retain vWF at high concentrations in their alpha granules. To study the effect of PEG on gradual loss or preservation a direct fluorescent antibody immunoflorescent staining protocol was developed. Slides were air dried for 5 min and immersed in 0.5% fresh paraformaldehyde in 10% PBS pH 7.3 for 10 min. Slides were soaked for 2 min in PBS with 5 changes. Subsequently excess PBS was drained and slides immersed for 2 min in ice cold dry acetone. Again, slides were drained and excess acetone was removed with 5 PBS washings of 2 min each. Slides were then immersed in 0.5% filter sterilized BSA in PBS and allowed to block overnight at 4° C. After draining excess block solution, 50 ul of primary antibody (Polyclonal rabbit anti-vWF-PB9062, Boster Biological Technology, Pleasanton, Calif.) at 5 ng/ml was applied immediately over the platelet spot and incubated in a humidity chamber for 4 hr at 4° C. Slides were washed with 5 changes of 0.5% BSA/PBS for 5 min each. Excess fluid was again removed and FITC labeled goatd anti-rabbit, Sigma F0382, was added 50 ug/ml in 0.5% BSA/PBS for 3 hr. Finally, after blotting excess fluid, slides were again washed with 5 changes of 0.5% BSA/PBS, drained, blotted, mounting medium was added, and the slides were cover-slipped. Slides were immediately photographed using a Leica DMIL photomicroscope and Leica LAS V3.8 image acquisition software. No post photographic image adjustments were made.

Platelet Binding to the Macrophage Like Cell Line U937.

U937 is a cell line derived from a patient with Acute Myelo-Monocytic Leukemia. It demonstrates several macrophage-like properties including expression of the Fc receptor. In this binding experiment 5 day old platelets from the blood bank are held in a standard storage media referred to as ACD on a flat-bed shaker under standard conditions of rotation. 'ACD' contains Adenosine, Sodium Citrate, and Dextrose. These platelets were split into two conditions, control and 2%/0 PEG-400, in a 12 well plate format with a final volume of 100 ul per well. All wells were incubated overnight at 5° C. All wells where then stained with fluorescein Diacetate (Sigma product F7378). This agent was protected from light and 1 mg was dissolved in 10 ml acetone and stored at −70° C. FDA was diluted 1:1000 in PBS immediately prior to use (Miyamoto el al., 2000.) All platelet wells received 2.5 ug final per well of fluorescein diacetate (FA) contained in 50 ul PBS. After 1 hr at room temp a further 100 ul of PBS was added and the 12 well plates were centrifuged at 3000 g for 20 min at RT. 150 ul excess fluid was carefully removed from all wells and discarded. Platelets were gently suspended. 100 ul of washed U937 cells, containing about $1\times10^4$ per ml, were added to all wells and incubated for 5 min at room temp. The plates were again centrifuged at 500 g for 5 min at 20° C. The excess fluid was carefully removed from the wells and the cells were covered with 25 ul glycerol based mounting medium and cover-slipped. Wells were examined and photographed with an inverted fluorescence microscope.

In Vitro Study of Cholesterol Membrane Mobility Using the Fluorescent Cholesterol Probe Filipin.

Filipin complex, (F9765 Sigma), was used to demonstrate intra-membrane distribution of cholesterol at 5° C. (Note 1: Stock solutions were prepared in DMSO that was rigorously dried with an equal volume of A-3 molecular sieve that had been regenerated at 300° C. overnight. The resultant filipin stock 25 mg/ml DMSO solution was prepared in a nitrogen atmosphere and frozen at −70° C. to limit water induced hydrolysis.)

Approximately 3 ml of residual pooled platelets were obtained after 72 hr at standard storage conditions. 100 ul of platelets were mixed with 100 ul of fresh filipin (300 ug/ml in PBS+10%, DMSO) in each of 12 wells of a 24 well cluster plate and incubated at room temperature for 35 min. (DMSO was included to assist with membrane loading of the highly insoluble filipin molecule.) All wells were then diluted by adding 2.5 ml of PBS and incubated another 15 min to dilute unbound filipin and allow removal of DMSO by dilution. The plate was next centrifuged at 2500 g for 20 min in a pre-warmed centrifuge at 22° C. All wells were gently aspirated and the PBS was replaced with 3 ml of control or test platelets as follows:

| Control (C) | 3 ml PBS |
| Test (P2) | 3 ml of 2% PEG-400 in PBS |
| Test (P4) | 3 ml of 4% PEG-400 in PBS |

All wells were next incubated 20 min at room temperature to allow DMSO to equilibrate. (Note: the final DMSO concentration in the Control wells or the PEG-400 only wells would be 6 parts in 10,000 or 0.06%.) Next the plate was held at 5° C. overnight and in the morning centrifuged in a 5° C. equilibrated centrifuge at 2,500 g for 20 min. Cold 4% Formalin/PBS was carefully added and the plate returned to 5° C. for overnight incubation. At 18 hr the plate was allowed to fix again at room temperature in the dark for 4 hours. Subsequently the formalin was aspirated and the plate washed with 4 changes of 2 ml of PBS. Finally, excess fluid was removed and the wells were photographed with an inverted fluorescent microscope. Note 2: Filipin is rapidly photo-bleached with the UV, thus the light intensity was lowered with a barrier filter of ~20% was used. This filter setting was used consistently for all photographs. All photographs were taken under the same camera conditions. No post photographic image alterations were made.

Studies of Platelet Storage Vs Platelet Function in a Mouse Model of Thrombocytopenia.

Fresh human platelets were obtained from the blood bank. These were pooled, mixed and divided twice to give 4 (new) platelet bags with 65 ml (+/−5 ml) in each. Next sterile PBS/PEG mixtures were made by adding filter sterilized PEG-400 (30% in PBS) serially diluting 1:4. (14 ml PBS+6 ml of PEG400=30% PEG, serially 1:4 diluted with PBS to give 7.5% PEG400, and 1.9% PEG400). Then, 10 ml of PBS or PBS/PEG was added into each platelet bag as follows: 10 ml PBS is 0 control=A; 10 ml of 1.9 is 0.25% peg final in platelets (a low dose tolerated by whole animal see below) =B; 10 ml of 7.5% gives 1% PEG-400 final (the max PEG400 dose tolerated by whole animal see below), =C; 10 ml of 30% gives 4% about 4 times the max dose tolerated in rhesus monkeys. Units were held at room temp 70 cycles/min, 1 inch stroke). The platelet units were confirmed to be negative for bacterial growth using 3 ml the platelet suspensions in Bactec blood culture bottles at 72 hr.

CD-1 outbred mice were obtained from Harlan Laboratories. All animals were pretreated with a 0.5 ml IP dose of 185 ug/mouse of filter sterilized fresh acetylsalicylic acid (aspirin) in PBS buffer. Fresh aspirin was used. Salicylate is the active metabolite responsible for most anti-inflammatory and analgesic effects; however, acetylsalicylate is the active moiety for the antiplatelet-aggregation effect and is rapidly hydrolyzed in water. On the following day all mice were given 3 U (heparin equivalents)/animal Lovenox (Enoxaparin Sodium Injection). After a 2 hr period for Lovenox to take full effect, the animals were given 100 ul platelets by IV tail vein injection, the platelets were allowed to circulate 20 min and the tail vein cut 1 cm from the tip with a new scapula for each animal. Bleeding was measured by collecting drops of blood for exactly 5 min on pre-weighed blotter paper Whatmen-40. The blotters were then weighed and these weights were compared using unpaired t test statistics. Platelets having an excessive amount of RBC in the units were sedimented under gravity in a 50 ml tube for 30 min and only the top 5 ml was harvested into a second 50 ml tube used for injection.)

Example 2

Preservation of Platelet Function

Preservation of platelet function was measured using in vitro methods and as further described below.

Experiment A:

Platelets are known to change shape and show partial aggregation when chilled. The goal of the initial experiments was to see if this behavior changed when platelets were incubated in the presence of PEG-400. Two standard random donor platelet concentrates, type O, were mixed by connecting the bags, followed by gravity mixing 8 times. This mixture was equally divided by weight into the two original platelet bags and either 10 ml of PBS or 10 ml of PEG-400 in PBS was added to the control and test unit respectively. The final concentration of PEG-400 in the unit was 2%. These units were then gently rotated at 70 cycles per minute, with a 1 inch stroke length, at 5° C., over 26 days. At the end of this time aliquots were examined and photographed.

PBS Control 2% PEG-400 in PBS

Results are shown in FIGS. 1A-B. Control platelets at 5° C. for 26 days can be visually compared to platelets stored with the addition of PEG-400 at 2% final concentration at 5° C. for 26 days. As shown in FIGS. 1A-B, the control was observed to be more aggregated and to have more rod shapes than the PEG test platelets. Additional experiments were conducted that showed similar results, and select results are shown in FIGS. 1A-B for illustration purposes.

Figure 2B:
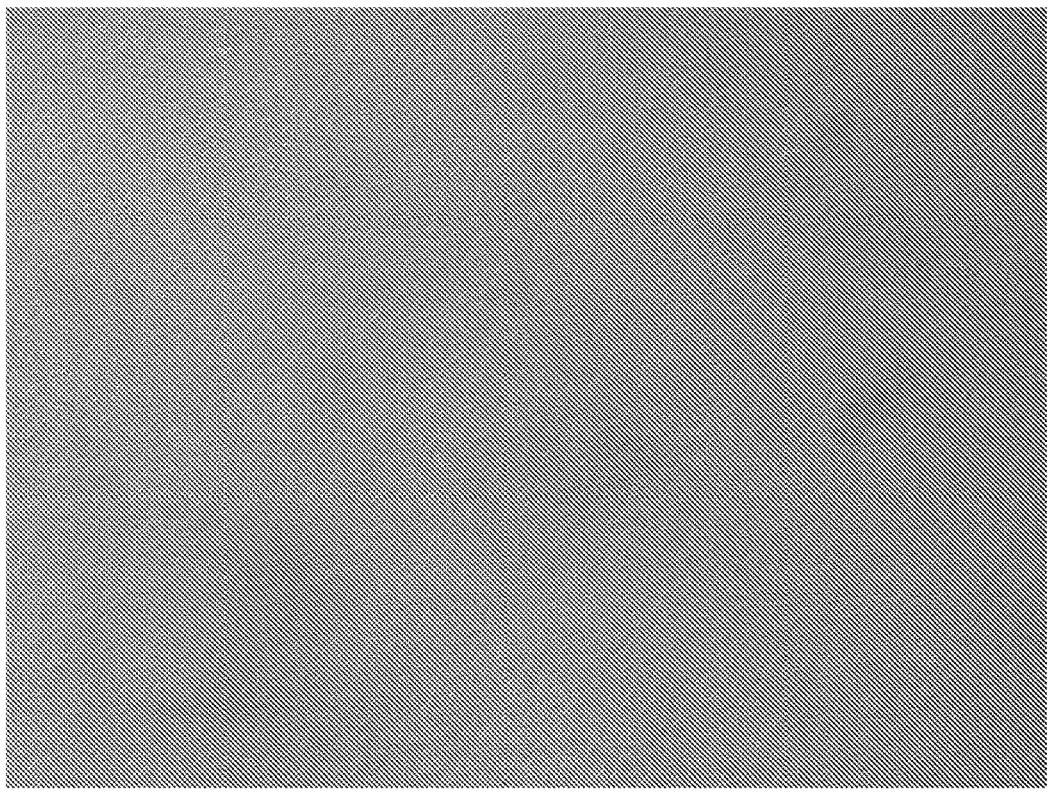

Experiment B:

In a second experiment a state of platelet 'aging' was induced using hydrogen peroxide. Hydrogen peroxide is not an agonist for the platelet receptor; however, exposure to hydrogen peroxide predisposes platelets to the "platelet storage lesion". In this study 2 day old residual platelets derived from one donor unit were tested by splitting the material in to a 24 well cluster plate. Control platelets had 10° % PBS added and were compared to test compositions with the addition of 10% volume PBS but containing 2% PEG-400, or 2° % PEG-400 plus 1% DMSO. Results are shown in FIGS. 2A-B. The differences in photographic exposure in FIGS. 2A-B are due to heavy precipitation of platelets with resultant clearing of the suspension resulting in less light diffusion in the 10% PBS control medium. As shown in FIGS. 2A-B, for platelets exposed to 10 hydrogen peroxide, the inclusion of 2% PEG400 in the media clearly resulted in less aggregation of the platelets. Images are shown in FIGS. 2A-B for illustrative purposes, and additional experiments were conducted that showed similar results. The platelets treated with 2% FEG-400 were observed to have less coarse clumping (aggregation), when compared to a matched control derived from the same platelet unit.

Experiment C:

Without wishing to be bound by any theory, the above observation of reduced aggregation in the presence of PEG suggested two possible hypotheses: one is that PEG may have prevented the effect of cold related aging, and the second is that the PEG may have blocked any agonist induced aggregation. Thus, additional experiments were performed to study epinephrine induced platelet aggregation following cold storage of platelets.

Fresh donor platelets were supplemented with PBS or PBS 2% PEG-400 as described in the methods, and incubated at 5° C. for 7 days. These control and test samples were then loaded side by side on a 96 well plate (ensuring that test and control reading would be made simultaneously). Control wells with zero epinephrine had only PBS added. Test wells had epinephrine in PBS added to give a final concentration of 10 ug/well. All loading of PBS or epinephrine agonist used a multichannel pipette to ensure test and control agents were added simultaneously. The plate was rotated in a humidity chamber overnight at room temperature. An ELISA plate reader was used to demonstrate changes in optical density at 690 nm in response to epinephrine challenge.

Results are shown in FIG. 3. As shown in FIG. 3, the control platelets failed to show any significant change in OD in response to epinephrine. This was observed based on the fact that cold stored platelets showed significantly higher baseline absorbency in the absence of epinephrine (see FIG. 3, Left hand bar under control platelets). Therefore the control platelets were "preaggregated" in the cold in the absence of any agonist. This is consistent with literature showing aggregation of platelets in the cold. The difference between 0 and 10 μg/ml epinephrine in the control platelets was not significant. Conversely, the PEG 2% stored platelets showed less initial aggregation in the stored state and showed a significant aggregation response to epinephrine.

Experiment D:

von Willebrand Factor (vWF) is a major component of platelet alpha granules. Intact functional platelets should retain these granules. Fresh platelets were divided into 6 aliquots of 4 ml each; 3 controls and 3 test aliquots were prepared by adding either 10% PBS (v/v) to controls or 10% v/v of 15% PEG400 in PBS to give a final concentration of 1.5% PEG400 in the test platelet aliquots. All aliquots were incubated at 5° C., +/−0.1, on a flat bead rotator with a 1 inch stroke at 70 cycles per min for 8 days. At 8 days 3 slides were prepared for both test and control samples using a cytocentrifuge at 2000 g for 2 min. Slides were then stained using anti-von Willebrand Factor DFA protocol in methods. After staining slides were immediately photographed using a Leica DMIL photomicroscope and Leica LAS V3.8 image acquisition software. No post photographic image adjustments were made to images analyzed.

Results are shown in FIGS. 4A-B. As shown in FIG. 4A, these results show that chilled control platelets show degranulation of vWF. Further, it also demonstrates that 1.5% PEG-400 was sufficient to prevent vWG degranulation at 5° C. (more bright green platelets were observed, indicating granules were retained; FIG. 4B).

Experiment E:

Chilled platelets are known to be rapidly removed from the circulation by fixed tissue macrophages of the reticuloendothelial system. Thus, an in vitro demonstration of platelet adherence to "macrophage-like" cells with or without the addition PEG-400 was performed. The AMMOL U937 cell line is a granulocytic/monocytic leukemia with some macrophage like properties including expression of the Fc receptor. Interestingly, von Willebrand factor of exceptionally high molecular weight (Mwt) is produced by megakaryocytes and is abundant in the Alpha granules of platelets. Reticuloendothelial "fixed" Fc receptors are thought to directly bind to capped (clumped) von Willebrand Factor, resulting in their clearance by fixed macrophages and other Fc receptor sites in the liver, spleen, lung, etc. (Olsson et al., 2005). In this binding experiment two units of 5 day old type O platelets from the blood bank were held in a standard holding media referred to as ACD on a shaker. 'ACD' contains Adenosine, Sodium Citrate, and Dextrose. These were split into two conditions and stained with a high level of fluorescein Diacetate (see Example 1, above, and Miyamoto et al., 2000).

Control conditions had standard 75 ul of ACD suspended platelets, plus 25 μl PBS in the control wells. Test conditions had 75 μl of ACD platelets, plus 25 ul of PBS/PEG-400 to give a final PEG-400 concentration of 2% PEG-400 in the test wells. Test and control wells were then held at 5° C. overnight on a flat-bed rotator. All wells were stained with a final of 2.5 μg Flouresine diacetate (FDA) per well for 1 hr at room temp. All wells were centrifuged at 3000 g for 20 min and excess fluid removed. The platelets were resuspended in 100 μl of PBS washed U937 cells (approx. $10^4$/ml) and incubated for a further 5 min at room temperature (RT). Cells were then spun at 500 g for 5 min at room temp. The excess fluid was again carefully removed from the wells and the cells covered with 25 ul of glycerol based mounting medium. Wells were examined with an inverted fluorescence microscope. Results 5 are shown in FIGS. 5A-C. The experiments were repeated and consistent results were observed as shown in FIGS. 5A-C.

Result:

Control platelets chilled to 5° C. overnight were adsorbed to the AMMOL/macrophage like cell line U937. In contrast under the same conditions and with matched platelets but following the addition of 2% PEG-400, only the faint staining of the U937 cells was seen and few heavily stained platelets were seen adherent to the cell surface. The degree of platelet adsorption to the U937 cell line was much less. This confirms a rapid time course for the 'cold platelet storage lesion'—in this example overnight storage at 5° C. was used. This study also demonstrates a 2% PEG-400 molecular weight (Mwt) composition that can substantially block adsorption of cold stored platelets to macrophage like cells.

Experiment F:

Cholesterol content of platelets has previously been shown to potentiate activation and lower platelet membrane fluidity (Sinha el al., 1977). This applies to platelets with high artificial cholesterol loading, to naturally occurring platelets from patients with hyperlipidemia, (Tomizuka el al., 1990), and to platelets derived from normal donors. (van Lier et al., 2008). The inventor thus wanted to study cholesterol behavior directly in platelet membranes in response to cold storage. The inventor hypothesized that the cold storage injury may be largely related, if not completely related, to physical clumping of high-cholesterol containing domains of the membrane. In the following studies membrane capping of cholesterol was visualized in an in vitro experiment, using the fluorescent cholesterol probe filipin. Filipin is a complex mixture of polyterpene compounds that mimic the structure of cholesterol. It is derived from *Streptomyces filipinensis* and is similar to the polyene antibiotic amphotericin B. Filipin is highly fluorescent and binds specifically to cholesterol. It is used as a histochemical stain for cholesterol in the diagnosis of Niemann-Pick disease, and will partition into cholesterol in vivo and in vitro. It has been used in living cells to study the raft/caveolae endocytosis pathway on mammalian astrocyte cells at concentrations of 3 µg/ml. (Pascual-Lucas et al., 2014).

Filipin complex (F9765 Sigma) was used to demonstrate intra-membrane distribution of cholesterol at 5° C. [Note 1: Stock solutions were prepared in DMSO that is rigorously dried with an equal volume of A-3 molecular sieve that had been regenerated at 300° C. overnight. The resultant filipin stock 25 mg/ml DMSO solution was prepared in a nitrogen atmosphere and frozen at −70° C. to limit water induced hydrolysis. Note 2: Filipin is rapidly photobleached by UV light, thus light intensity was lowered with a barrier filter ~20%. This filter setting was used consistently for all photographs. All photographs were taken under the same camera conditions. No post photographic image alterations were made.]

Approximately 3 ml of residual pooled platelets were obtained after 72 hr at standard storage conditions. 100 µl of platelets were mixed with 100 µl of fresh filipin (300 ug/ml in PBS+10% DMSO) in each of 12 wells of a 24 well cluster plate and incubated at room temperature for 35 min. (DMSO was included to assist with membrane loading of the highly insoluble filipin molecule.) All wells were then diluted by adding 2.5 ml of PBS and incubated another 15 min to dilute unbound filipin and allow removal of DMSO by dilution. The plate was next centrifuged at 2500 g for 20 min in a pre-warmed centrifuge at 22° C. All wells were gently aspirated and the PBS was replaced with 3 ml of control or test storage solution as follows:

| Control (C) | 3 ml PBS |
| Test (P2) | 3 ml of 2% PEG-400 in PBS |
| Test (P4) | 3 ml of 4% PEG-400 in PBS |

All wells were again incubated 20 min at room temperature to allow DMSO to equilibrate. (Note: the final DMSO concentration in the Control wells or the Peg-400 only wells would be 6 parts in 10,000 or 0.06%.) Next the plate was held at 5° C. overnight and in the morning centrifuged in a 5° C. equilibrated centrifuge at 2,500 g for 20 min. Cold 4% Formalin/PBS was carefully added and the plate returned to 5° C. for overnight incubation. At 18 hr the plate was allowed to fix again at room temperature in the dark for 4 hours. Subsequently the formalin was aspirated and the plate washed with 4 changes of 2 ml of PBS. Finally, excess fluid was removed and the wells were photographed with an inverted fluorescent microscope. Results are shown in FIGS. 6A-C.

Figure 6A:
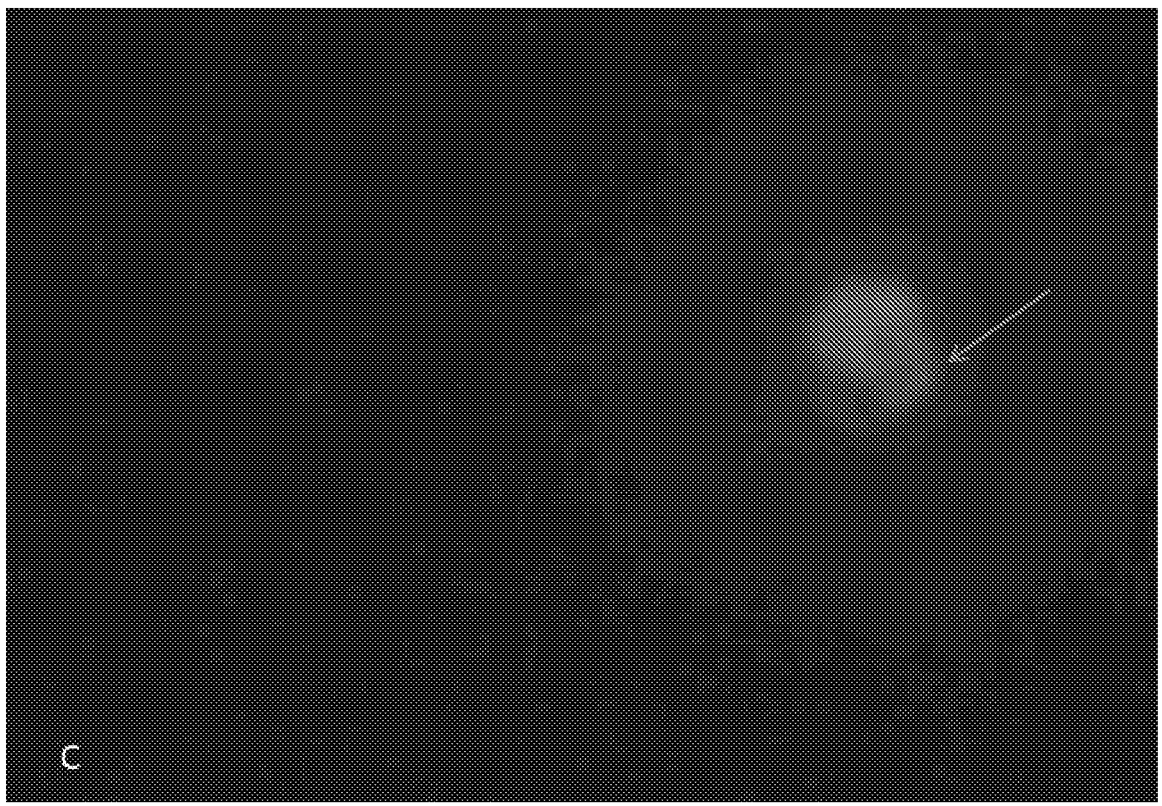
FIGS. 6A-C.
Figure 6B:
Figure 6C:
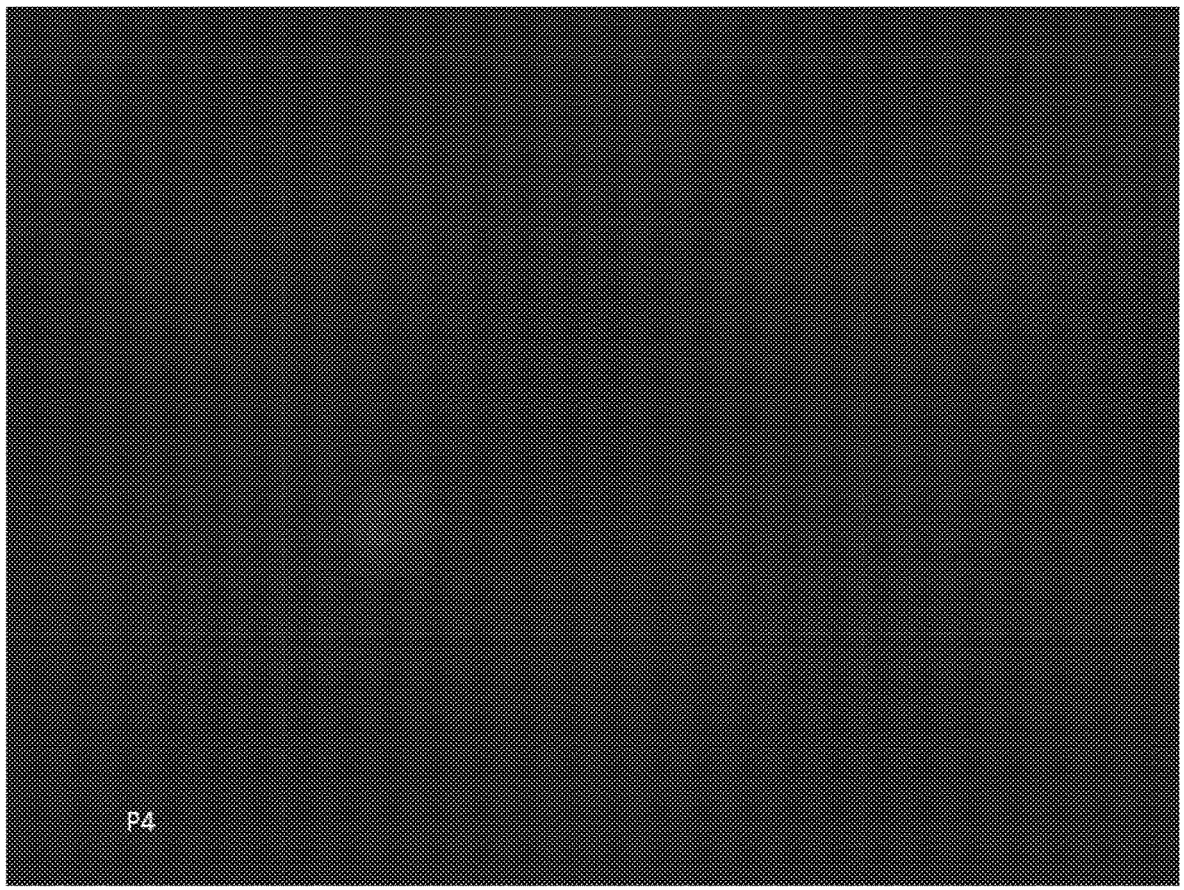

Results:

Controls show accumulation of the cholesterol probe filipin in clusters around the platelets membranes (FIG. 6A). Treatment conditions with 2% PEG-400 (FIG. 6B) show less filipin clustering, as do treatment conditions with 4% PEG (FIG. 6C). Additional images were obtained that were consistent with these results.

The results of the above in vitro experiments replicate previous findings that cold conditions (here 5° C., +/−0.1) are sufficient to induce platelet aggregation, loss of receptor agonist interaction, adsorption to macrophage like cells, and degranulation as measured by the loss of vWG granules. A surprising finding shown in the results is that the inclusion of a relatively narrow range of low molecular weight PEGs, in a particular range of w/v %, in storage solutions was sufficient to substantially block these 'cold storage lesion' effects. Further, the inventor observed cholesterol capping under cold storage conditions. Without wishing to be bound by any theory, since capping is frequently associated with signal transduction and since the above late effects (aggregation, degranulation) require signal transduction (Zolla et al.), the results support the idea that cholesterol capping under cold storage is sufficient to recapitulate all features of the cold storage lesion and that enhancing cholesterol mobility with low molecular weight PEG is sufficient to reverse all features of the cold storage lesion effects.

Example 3

Preservation of Platelet Function In Vivo

Preservation of platelet function was observed in vivo using a mouse animal model. The results of the below experiments show that treatment of platelets with a storage media containing PEGs of various molecular weights and final % composition can prolong platelet function as demonstrated as in an in vivo mouse model.

Figure 7:
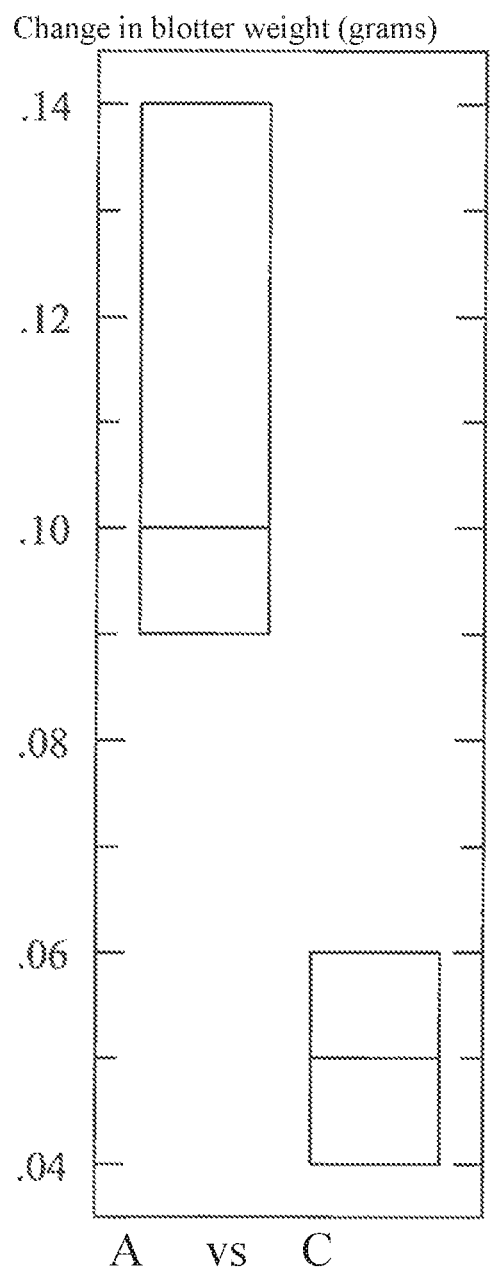
FIG. 7: Change in blotter weight (grams). Results for A=0 PEG control vs. C=1% PEG-400 (P=0.021) are shown. Low grams of blood documents less bleeding.

Briefly, the animal model experiments were performed as follows. Fresh human platelets were obtained from a blood bank, consisting of 3 ABO 'O' units and 2 ABO 'A' units. These were pooled, mixed and divided twice to give 4 (new) platelet bags with 75 ml (+/−5 ml) in each. Next sterile PBS/PEG mixtures were made by adding filter sterilized PEG-400 (30% in PBS) serially diluting 1:4. (14 ml PBS+6 ml of PEG=30% PEG, serial ¼ diluted with PBS to give 7.5% PEG, and 1.9% PEG400). 10 ml of PBS or PBS/PEG was then added to each platelet bag as follows. As shown in FIG. 7, 10 ml of PBS is the 0 control=A; 10 ml of 1.9 is 0.25% peg final in platelets (a low dose tolerated by whole animal see below)=B; 10 ml of 7.5 gives 1% PEG-400 final (approximately the max PEG400 dose tolerated by whole animal see below), =C; 10 ml of 30% PEG400 gives 4% PEG400 final, about 4 times the max dose tolerated in rhesus monkeys. Units were held at room temp 140 cycles/min, 0.5 inch stroke). The platelet units were confirmed as negative for bacterial growth using 3 ml in Bactec blood culture bottles at 72 hr.

CD-1 outbred mice were obtained from Harlan Laboratories. All animals were pretreated with a 0.5 ml IP dose of 185 µg/mouse of filter sterilized fresh acetylsalicylic acid in PBS buffer. On the following day all mice were given 3 U (heparin equivalents)/animal Lovenox. (Note: Aspirin was fresh. Salicylate is the active metabolite responsible for most anti-inflammatory and analgesic effects; however, acetylsalicylate is the active moiety for the antiplatelet-aggregation effect and is rapidly hydrolyzed in water. After a 2 hr period for Lovenox effect the animals were given 100 ul platelets by IV tail vein injection, the platelets were allowed to circulate 30 min and the tail vein cut 1 cm from tip with a new scapula for each animal. Bleeding was measured by collecting drops of blood for exactly 5 min on pre-weighed blotter paper Whatmen-40. The blotters were then weighed and these weights were compared using unpaired t test statistics. Platelets containing an excessive amount of RBC in the units were sedimented under gravity in a 50 ml tube for 30 min and only the top 5 ml was harvested into a second 50 ml tube used for injection.

Experiment A:

Platelets were pooled (11 day old platelets) Obtained 4 type 'O' platelet units from the blood bank. Mixed and divided platelets again into 4 equal 95 ml aliquots in platelet unit bags. These pooled platelets contained ACD. Supplemental storage agent were added as follows:
A=pbs control
B=pbs+0.2% PEG-400, final
C=pbs+1% PEG-400, final
D=pbs+3% PEG-300, final placed on a rotator at room temp (24° C.).
On day 11, gave 0.3 mg salicylic acid IP
On day 12, gave 0.5 ml 3 units heparin IP
Waited one hr.
And then injected platelets
Waited 15 min for injected platelets
to recover function In situ . . .
Then snipped tail—blotted 5 min+−30 sec
Statistical Analysis:

As shown in FIG. 7, a graphic BOX plot is provided showing 50% of values within the box with a median line and 25% in each wing. Any included outliers are shown as a dot with an open circle around it. Any excluded outliers are shown as large black circles. (John Tukey outlier method. Similar to mean and SD describing a distribution, here outliers are defined relative to the median as either 3 Inter-Quartile Range (IQR) or more above the third quartile or 3×IQR or more below the first quartile.)

Figure 8:
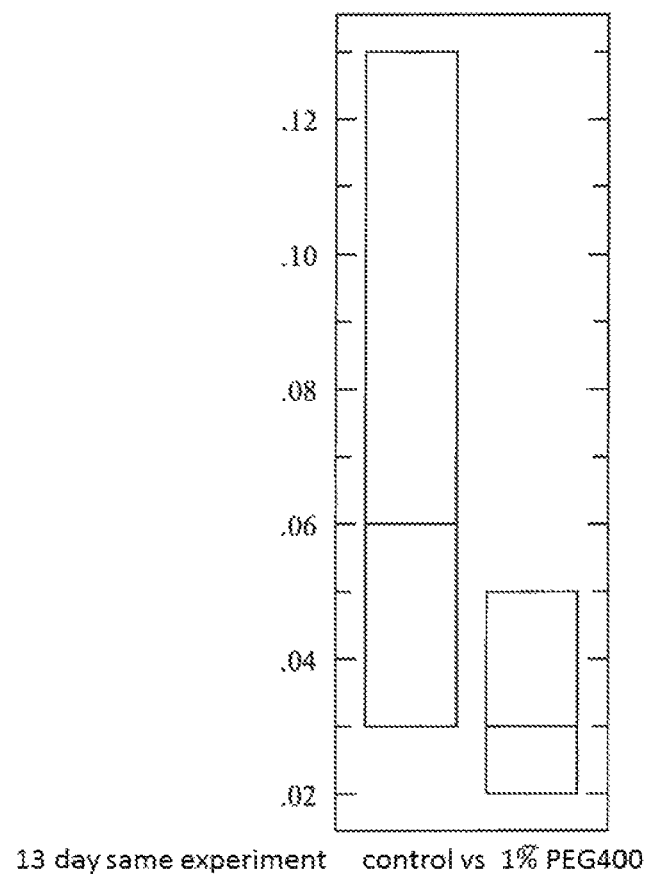
FIG. 8: Change in blotter weight (grams). Are shown for the 13 day experiment. PEG control data is shown on the left and the 1% PEG400 data is shown on the right.

Experiment B:

The experiment was repeated at day 13 (13 day old platelets) using the same platelet units and same conditions and using 6 additional animals. Variability was very high due to difficult injections. The experiment did not reach significance due to low numbers and high viability, but shows a trend similar to the first experiment. Results are shown in FIG. 8.

Figure 9:
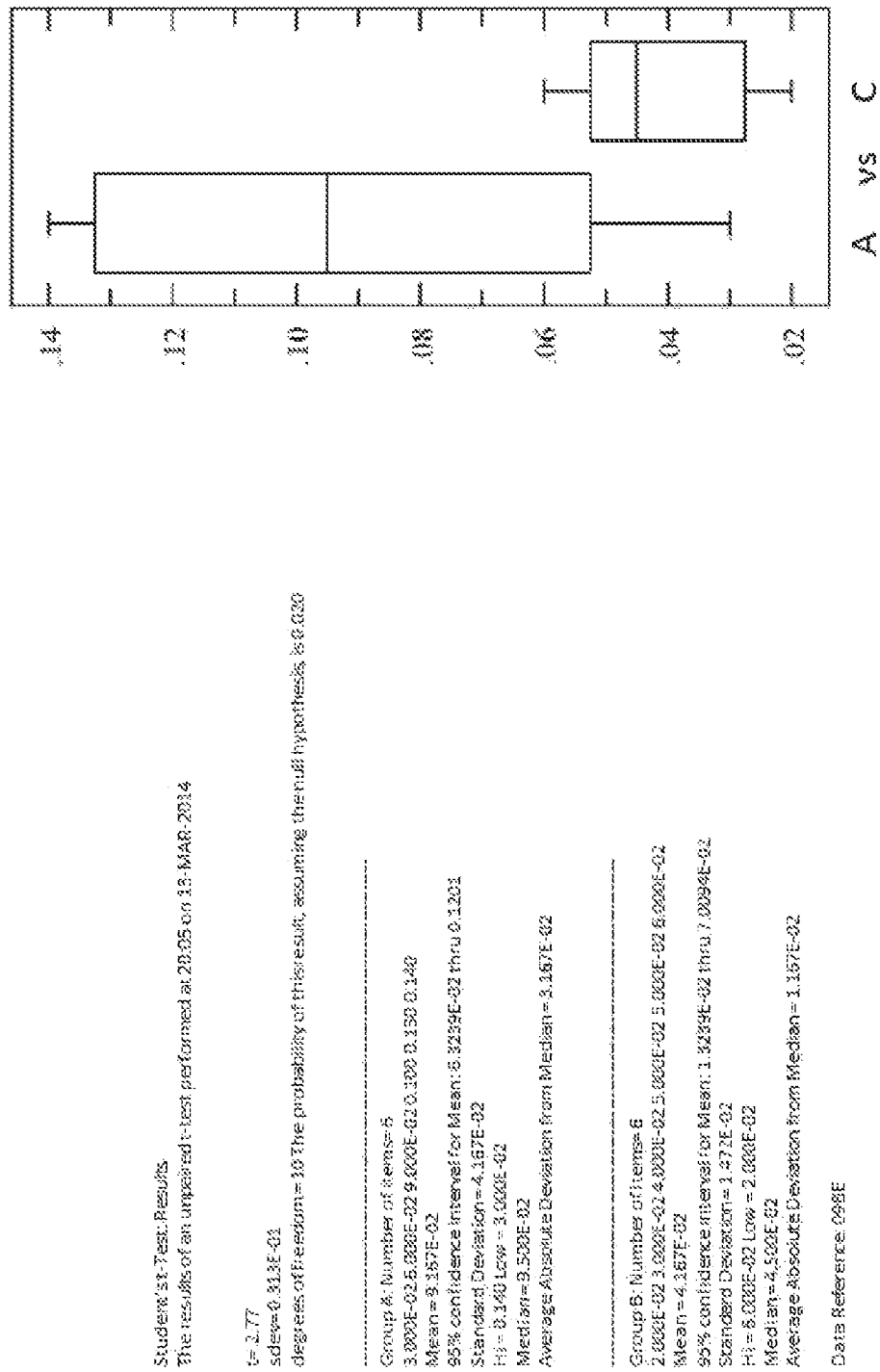
FIG. 9: Combined data from day 11 and day 13. The addition of 1% PEG-400 ("C") showed significantly more clotting as compared to the control storage solution ("A"). (P=0.02).

For further statistical analysis the day 11 and day 13 data were combined since conditions are closely matched, and the results are shown in FIG. 9. As shown in FIG. 9, the addition of 1% PEG-400, "C", shows significantly more clotting vs the standard platelet storage condition. (P=0.02).

Experiment C:

Bleeding control using the same pretreatment conditions and one day old platelets under standard conditions vs no platelets. Results are shown in FIG. 10.

| | Day 1 platelets Result |
|---|---|
| N | 3 controls vs 3 max bleed |
| Ave | 0.007 vs 0.07 blotter weight in grams |
| Sd | 0.05 vs 0.05 Standard deviation in grams |

Figure 10:
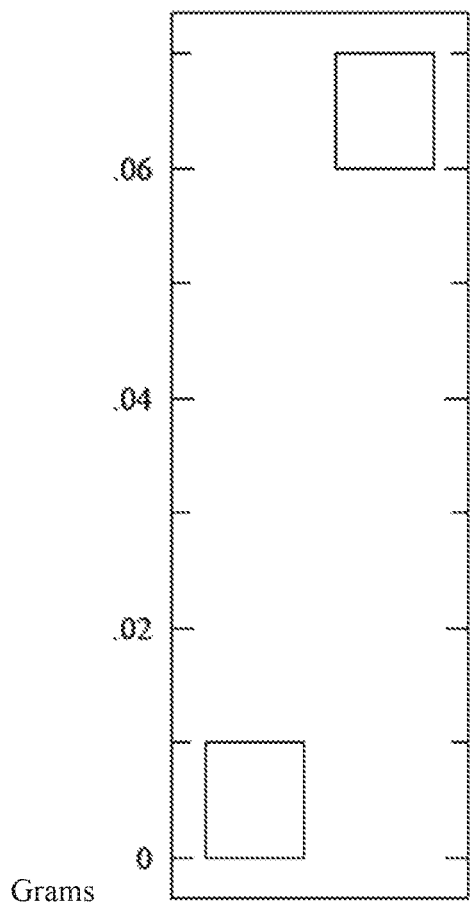
FIG. 10: Results for Control platelets and No platelet intervention are shown (P=0.0002).

As shown in FIG. 10, this data confirms that at 1 day old platelets stored under standard conditions are functional and that the maximum bleeding as demonstrated by the zero platelet group is consistent with prior studies.

Experiment D:

It was not feasible to evaluate more than two groups of mice during any one experiment. Therefore 0.25% PEG-400 and 4% PEG-400 were not further investigated. In experiment D 1% PEG-400 in PBS was again used as the test condition and again compared to a matched control derived from the same platelet unit, but with only the addition of an equal volume of PBS.

5-11 actual—two apheresis units of 48 hr age were received. They were rotated under standard conditions:
70, 1 inch stroke cycles per min at 22-25° C. They were Both O and both were rejected by the blood bank due to hepatitis B Core antibody positive status.

Each apheresis recovers a higher number of platelets. One apheresis unit is equivalent to ~7 Random donor platelet concentrates. The material was divided into 6 platelet storage bags using 60 ml syringe and 16 g needle to transfer 60 ml of platelets slowly (1 min) into new unit bags. Unit A was used to make room temp control and room temp PEG 1% test units. Unit A was also used to prepare 5° C. control and 5° C. PEG 2% test units.

The room temperature pair was tested again at 11 days to demonstrate reproducibility. The 5° C. storage pair was tested at 23 days because it was suspected that they could be functional based on in vitro observations.

Figure 11:
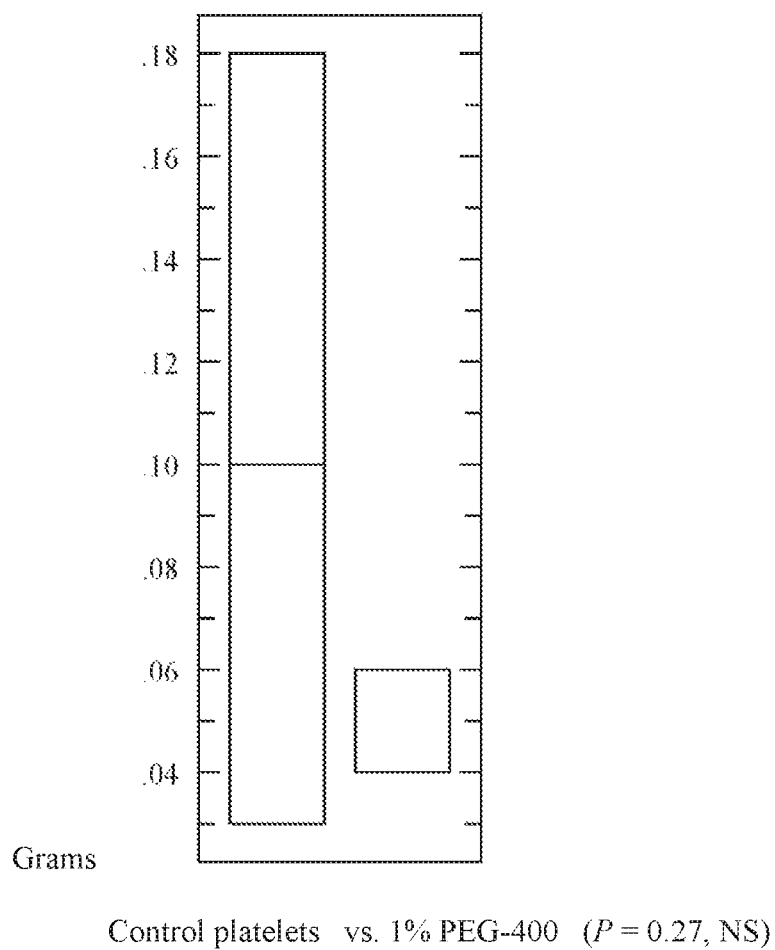
FIG. 11: Results for Room temperature control and test platelets again at 11 days are shown.

Results are shown in FIG. 11. Room temperature control and test platelets again at 11 days. As shown in FIG. 11, the experiments showed high variability but the observed trend was similar.

Figure 12:
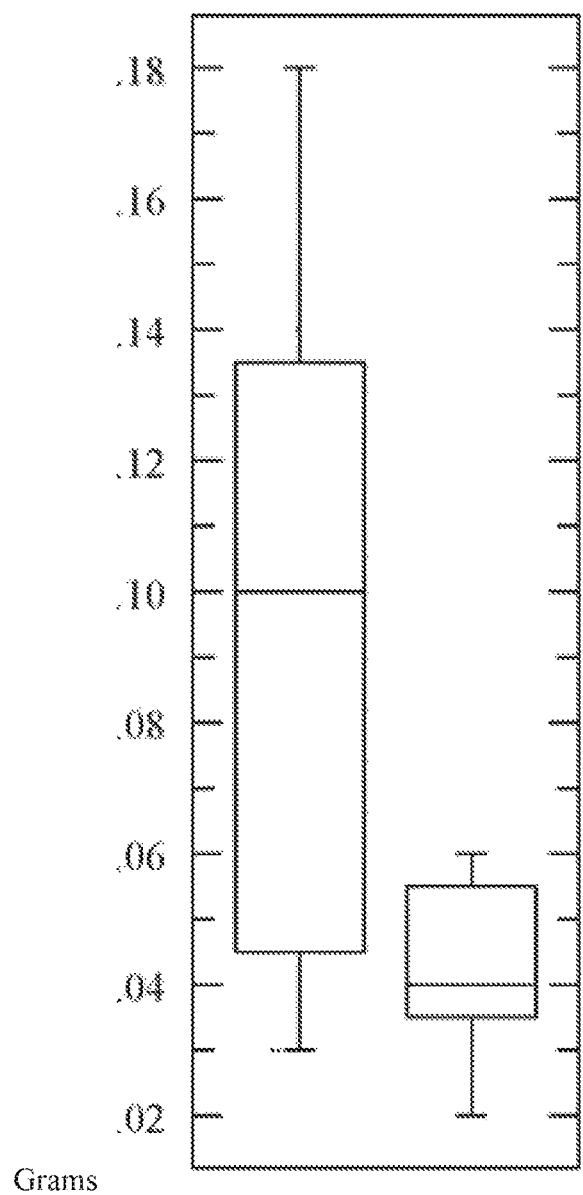
FIG. 12: Combined 11-13 day Room Temperature results.

Combined 11-13 day room temperature results were combined and are shown in FIG. 12.

Experimental conditions were closely matched so results may be combined to overcome the small number of animals in each group. (N=3) Combined data were from prior experiments day 11, day 13, and day 11. All controls and tests were at room temperature (RT) with paired platelet source vs PEG-400 1%, and pretreated with aspirin (−24 hr) and 3 iu Lovenox (−1 to 5 hr). Following injection, a delay of 15 min was allowed to occur so that platelets could circulate in all animals to allow for recovery of function of platelets. The tail vein was again cut 1 cm from the tip and the blood collected for 5 min.

Results: Weight of blood after tail vein cut is given in grams for combined 11 day groups.

TABLE 3

| Control (pbs) Room temp. | vs. | PEG (1% PEG-400 in PBS) at Room temp. | |
|---|---|---|---|
| .03 control | .04 | PEG | (May 23, 2014 group, |
| .18 | .04 | | P = 0.27) |
| .1 | .06 | | |
| .1 | .04 | | (Mar. 11, 2014 group, |
| .14 | .05 | | P = 0.021) |
| .09 | .06 | | |
| .13 | .05 | | (Mar. 13, 2014 group, |
| .06 | .03 | | P = 0.027) |
| .03 | .02 | | |

Analysis of combined data:

| Controls | vs | 1% PEG-400 | |
|---|---|---|---|
| N = 9 | | N = 9 | |
| X = 0.095 | | X = 0.043 | |
| SD = 0.05 | | SD = 0.013 | P = 0.008 |

Conclusions:

1) The difference between control platelets and PEG platelets is reproducible. 2) PEG platelets are active at day 11-13. 3) Profound anticoagulation appears associated with high variability in bleeding in the controls as determined by weight method.

Figure 13:
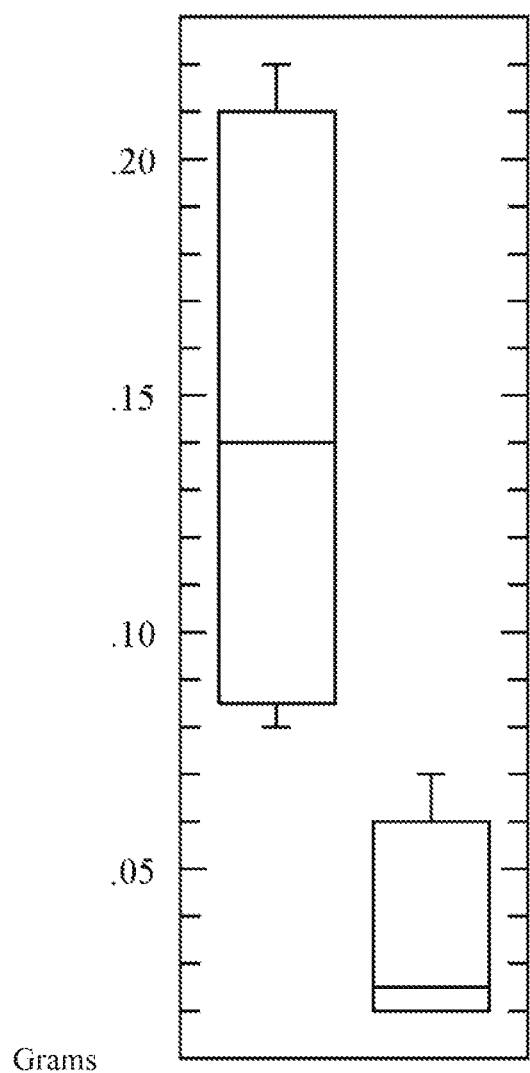
FIG. 13: Data for Control 5° C. standard vs. 5° C. 2% PEG-400 platelets at 19 days are shown (P=0.014).

Experiment E:

Day 19, 5° C. control platelets vs 5° C. 2% PEG-400 test platelets. The experimental set up was very similar to previous with minor differences in timing. 0.3 ml of 1.8 mg/ml aspirin was given at about 1:00 (made fresh 1:10 from −70° C. 18 mg/ml stock in PBS) The next day—0.5 (5 units) Lovenox was given at about 12:30. The experiment was started 2 hr later. 30 ml of both platelet groups was sedimented for 45 min at 4° C. to remove any aggregated clumps. (None were visible.) 4 ml from the top was removed as the experimental test and control materials. After injection the platelets were allowed to circulate for 20 min. The tail vein was then cut 1 cm from the tip and allowed 6 min bleeding with collection of drops on pre-weighed Whatman—40 blotter paper. (#4—thick). Results are shown in FIG. 13.

Conclusion: The inclusion of 2% final concentration of PEG-400 Mwt in the standard ACD platelet storage medium allowed 19 days of storage at 5° C.+/−0.02° C., with mixing on a flat-bed shaker with a 1 inch stroke diameter and 70 cycles per min continuous shaking.

Figure 14:
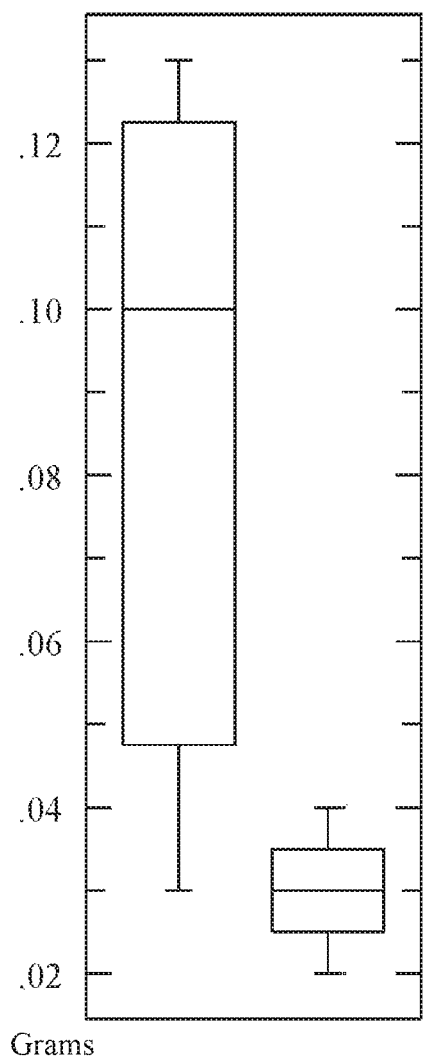
FIG. 14: A Box plot of 5° C. control platelets vs. 5° C., 2% PEG-400 platelets 26 days is shown.

Experiment F:

5° C. Control platelets vs. 5° C. 2%, PEG-400, platelets after 26 days of shaking. All animals got 0.3 ml of 1.8 mg/ml aspirin I.P. on 6/6/14 and 0.5 ml of 10 iu/ml lovenox IP, 2 hr prior to platelet injection on 6/7. 0.1 ml of test or control platelets were given by IV tail vein injection and allowed to incubate in the animals for 20 min then the terminal 1 cm of tail vein was cut with a scalpel and blood collected on blotter paper 6 min. (Both control 5° C. platelets and peg 5° C. platelets were sub-cultured on chocolate agar and no growth was seen at 48 hr.) Results are shown in FIG. 14.

Conclusions:

Modified platelet storage conditions using 2% final weight of PEG-400 added to the standard ACD platelet storage units and rotated on a flat-bed shaker with at 1 inch diameter stroke and 70 cycles per minute at 5° C. successfully preserved platelet function for 26 days. Control platelet, receiving only PBS were dysfunctional.

Summary of Animal Model Results:

A thrombocytopenic mouse model was used to assess the functional status of stored platelets. In patients with coagulopathies most hospitals offer a clinical "bleeding time" assay. The bleeding time assay is used to make an integrated assessment of all elements required for thrombostasis. In patients with a coagulopathy the patient's ability to accomplish hemostasis—regardless of the specific coagulopathy or defect—can be measured by the bleeding time. The bleeding time is performed by making six small standardized cuts in the skin of the arm and counting the number of seconds until bleeding stops. Although in vitro studies can model some elements of platelet function, many elements—such as thrombin binding and clot retraction—cannot yet be duplicated. Thus, the bleeding time assay is still necessary. In a similar way, while the current in vitro studies demonstrate known defects in aged or cold stored platelets (aggregation, macrophage adherence, etc.), they do not confirm that the new storage conditions can be used to provide functional platelets in vivo.

There are three elements that may be important to understanding the above animal model results, as follows: (1) Why aspirin was used, (2) why Heparin was used, and (3) why the mice were incubated for 15 to 30 min prior to bleeding. In the above animal model a simple IP injection of acetylsalicylic acid was given one day prior to the study. The dose can inactivate the cyclooxygenase pathway of mouse platelets. Similar to humans, the cyclooxygenase of circulating mouse platelets is permanently poisoned by aspirin and platelet function is only slowly restored by the production of new platelets. At the dose used, the half-life of aspirin in the blood stream of the mouse has been measured at 30 min to 1 h. Thus, 20 to 40 half-lives are available to remove unbound aspirin from the mouse prior to giving human platelets the next day. Thus, mouse platelet function may be eliminated and following injection human platelet function can be demonstrated. Second, a high dose of Lovenox, a synthetic long-lived heparin-like molecule to arrest the classical thrombin/fibrinogen coagulation cascade, was given. This suppression is predicted to peak at 1 to 3 hrs following IP Lovenox, based on the half-life of 5 to 7 hr. Again, when the stored human platelets were administered, they were substantially the only factor remaining to assist coagulation of these mice. Third, the platelets were allowed to circulate for 15 to 30 min in the above experiments. This allowed damaged or aggregated platelets to be removed and PEG to elute from platelets—and this models the anticipated human therapeutic pattern of use. Note: the blood volume of a 30 g mouse is ~2 ml and thus the 100 ul dose represents 5% of murine blood volume. Humans typically receive 4 to 7 units of random donor units at one transfusion corresponding to 5 to 9% of blood volume. In this context, the animal model provides strong evidence of functional thrombocyte transfusion after 26 days of storage in a practical dosing context. Further, refrigeration may avoid the need for bacteriologic assessment, and may facilitate overnight transport of platelets from areas of excess to areas of need.

The above data demonstrates that ACD storage solution can be supplemented with PEG-400 to give a more effective storage solution. Effective platelet function was shown at room temp out to 13 days at room temperature. Successful platelet storage with retention of function using these compositions was also observed out to 26 days at 5° C. The agents used have a beneficial effect on platelets storage when tested in an animal model, extending platelet storage life to at least 13 days under room temperature storage and 26 days under 5° C. storage.

Example 4

Compositions and Compounds for Enhanced Storage of Platelets

In addition to the improvements observed with PEG as demonstrated in the above examples, the inventors observed improved platelet preservation when certain additional compounds were added to the storage solution. As demonstrated below these compounds were included in the media in a particular range of doses, and an enhancement of platelet function was observed.

The following methods were used: "Fresh" in-date 2 day old blood bank O pos random donor platelets were recovered from segments and held in a 50 cc tub with rotation 22° C., 70 cycles/min 1 inch stroke) for 30 min. Glycerol (Fisher tissue grade product) was obtained from virology diluted to 50% in sterile saline and filter sterilized. 12 g glycerol were added to 12 ml sterile saline (BioMeriux—vitek saline) and mixed. This mixture was filter sterilized using a 0.45 um filter (CELLULOSE ACETATE). Dilutions were made of the above saline to a concentration 50%, 25%, 12%, 6%, 3° %. 200 ul of platelets were withdrawn slowly (8 sec) and add slowly to 7 sterile 2 ml microcentrifuge tubes. 200 ul of 50%, 25%, 12% 6%, and 3% glycerol/saline and two controls using 200 ul saline, were then added to the platelets with slow mixing. Thus the final glycerol concentrations=25, 12, 6, 3, and 1.5. These aliquots were allowed to rotate at room temp as above for 5 min and then placed on a rotator at 70 cycles/min with a 1 inch stroke at 5° C. (temp previously equilibrated and documented at 5° C.)

Results:

At day 3, dark dense platelets were observed, indicating degranulation in the control groups (in both control groups A & B). A variation in platelet size was observed: small and dense indicating degranulation, vs. normal morphology pale plump platelets without the dense small degranulated appearance. Degranulation in response to cold storage is associated with the first step of the platelet activation GP-1 signal resulting in α-granule degranulation and massive extracellular release of vWF. (Suhasini el al., 2010). Table 4 presents a summary of additional cryoprotective agents scored for the effect on microscopic degranulation (20× high contrast lighting as above).

TABLE 4

Studies of the effect of cryoprotective on platelet degranulation.

| Agent* | Mwt | Days at 5° C | 6% | 3% | 1.5% | 0.75% | 0.38% | Control^ |
|---|---|---|---|---|---|---|---|---|
| Glycerol propoxylate | 266 | 6 | NT | none | fair | fair | none | none |
| Trimethylopropane ethoxylate | 450 | 6 | NT | none | none | none | none | none |
| Pentaerythritol ethoxylate | 270 | 6 | NT | none | none | none | none | none |
| Pentaerythritol Propoxylate | 426 | 6 | NT | none | none | none | fair | none |
| Methoxy PEG | 350 | 6 | NT | good | good | none | none | none |
| Glycerol | 92 | 10 | good | fair | NT | NT | NT | none |

*Final concentrations of cryoprotectants are shown as % solution in ACD-Platelet mixture.
NT, Not tested.
, Results - None = no effect detected ~90% complete degranulation, Fair = 25 to 50% of platelets are non-degranulated. Good = >80 are non-degranulated.
^Controls were made in the same manner as test solutions by mixing ACD PBS containing zero cryoprotectant with test platelets in a 1:1 addition. After 10 min rotation at room temp all samples were transferred to 5° C. and rotated together.

Figure 15A:
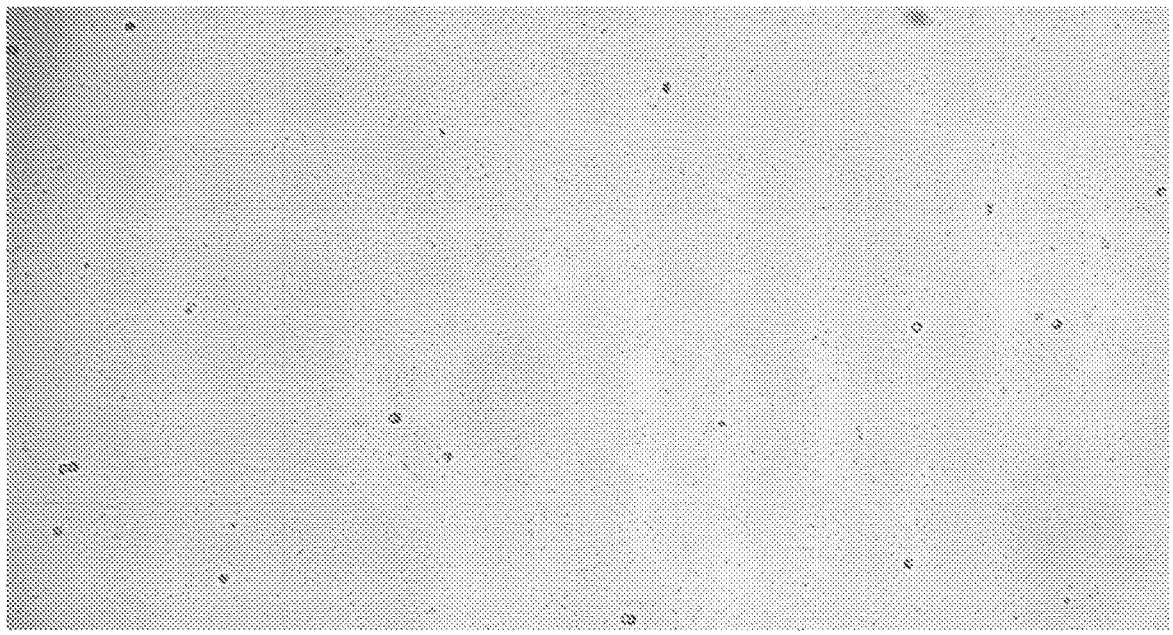
FIGS. 15A-B: Platelets stored in media containing 6% glycerol (FIG. 15A) and a matched control of platelets stored in a media without glycerol (FIG. 15B) are shown.
Figure 15B:
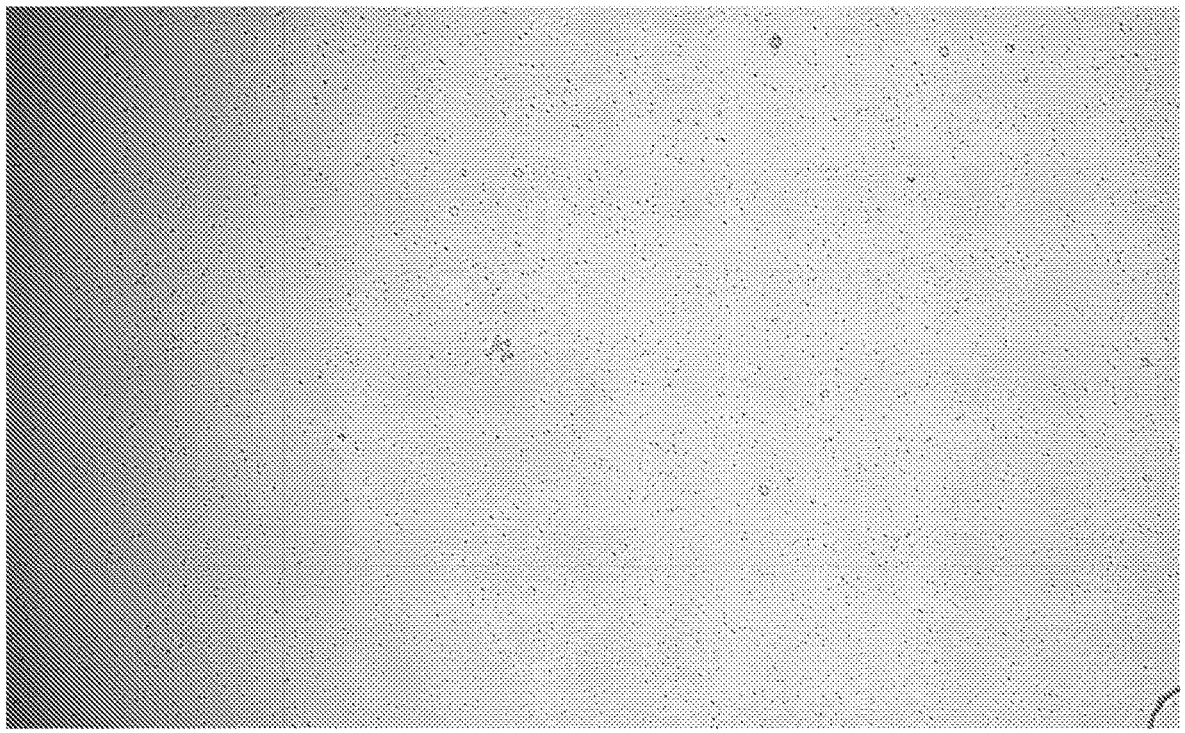

Results are shown in FIGS. 15A-B.

When 3% glycerol was included in the media, at day 3, a light color of platelets was observed, indicating granule preservation (in both 3% glycerol groups A & B).

At day 6, for the control groups, dark dense platelets were observed, indicating degranulation (for both control groups A & B).

When 3% glycerol was included in the media, at day 6, a light color of platelets was observed, indicating granule preservation (in both 3% glycerol groups A & B).

At day 10, for the control groups, dark dense platelets were observed, indicating degranulation (for both control groups A & B).

When 3% glycerol or 6% glycerol was included in the media, at day 10, a light color of platelets was observed, indicating granule preservation (in both the 3% glycerol groups A & B).

Conclusion:

3% and 60/% glycerol, in a suitable physiologic aqueous solution, prevented 5° C. induced degranulation at 3, 6, and 10 days. These data support the idea that this biologically well tolerated compound may thus be used or included in platelet storage solutions, e.g., at a 1% to 12% final concentration. Without wishing to be bound by any theory, these results support the idea that the glycerol may act as a cryoprotectant towards platelets.

The inventors anticipate that the following compounds may also be used to enhance platelet storage when used at 1% to 40% of their normal cryoprotectant levels (i.e., at 0.1% to 6% final concentration): glycerol propoxylate (mwt 266), trimethylolpropane ethoxylate (mwt 450), pentaerythritol propoxylate (mwt 426), pentaerythritol ethoxylate (mwt 270).

Further, there is a likelihood that PEG 400 (0.3 to 3%) or PEG 350 (0.3 to 4%) can be advantageously combined with the lower concentration range of the cryoprotectant agents listed below with all possible permutation of the above concentrations, except that even lower levels of glycerol, glycerol propoxylate, trimethylolpropane ethoxylate, pentaerythritol propoxylate, and/or pentaerythritol ethoxylate, could be advantageously used. Without being bound by theory, the inventors anticipate that pentaerythritol propoxylate may be particularly useful at preserving transmembrane proteins, including pore structures with hydrophobic domains during the process of protein crystallization. This property supports the idea that combinations using the demonstrated cholesterol disaggregating/lipid bilayer penetrating properties of low molecular weight PEG with pentaerythritol propoxylate may be used to achieve a synergy of functional stabilization at concentrations well below the typical levels used for cryopreservation and crystallization. The inventors anticipate that the combination of a PEG as described herein synergize with when used in combination with pentaerythritol propoxylate.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Patent Publication No. 2009/0191537
Patent Publication No. 2012/0107791
U.S. Pat. No. 5,358,844
U.S. Pat. No. 8,052,667
WO1985002116
Barkalo K., Hartwig J. H. The role of actin filament barbed-end exposure in cytoskeletal dynamics and cell motility. Biochem. Soc. Trans., 23; 451-456, 1995
Chernoff et al., The cellular and molecular basis of the platelet storage lesion. *Transfusion V* 32(4): 386-390, 1992.
Devine et al., The Platelet Storage Lesion. *Clinics in Laboratory Medicine* 30:475-487, 2010.
Egidi et al., Troubleshooting in platelet storage temperature and new perspectives through proteomics. [review] *Blood Transfusion* 8:(Suppl 3); s73-s8, 2010.
Fujimoto et al., 2003.
Hogman, C. F., New trends in the preparation and storage of platelets. *Transfusion* 32 (1): 3-6, 1992.
Holm S. Storage and quality assessment of platelets. [review] *Vox Sanguinis* 74:207-216, 1998.
Insel, P A, Nirenberg P, Turnbull J, Shattil S J. Relationships between Membrane cholesterol, alpha-adrenergic receptors, and platelet function. *Biochemistry* 17(24):5269-73, 1978
Kaushansky K. "Lineage-specific hematopoietic growth factors". *N. Engl. J. Med* 354 (19): 2034-45, 2006.
Lier et al., Role of membrane cholesterol in platelet calcium signalling in response to VWF and collagen under stasis and flow. *Thromb Haemost;* 99(6):1068-78, 2008.
Lockard J S. *Epilepsia* 20:77-84, 1979.
Miyamoto et al., Establishment of Fluorescein diacetate and ethidium bromide assay for quality assessment of isolated islets. *Cell transplantation* 9:681-86, 2000.
Olsson et al., Platelet homeostasis is regulated by platelet expression of CD47 under normal conditions and in passive immune thrombocytopenia. *Blood;* 105:3577-3582, 2005.
Pascual-Lucas et al., LPS or ethanol triggers clartrin rafts/caveolae-dependent endocytosis of $TLR_4$ in cortical astrocytes. *J Neurochemistry* 2014, 129:448-462.
Sinha et al., Cyclic AMP Metabolism in Cholesterol-rich Platelets. *Journal of Biological Chemistry* 252; (10): 3310-3314, 1977.
Suhasini K, et al. A revised model of platelet aggregation. *J Clin Invest* 105:783, 2010
Sungaran et al., The role of platelet a-granular proteins in the regulation of thrombopoietin messenger RNA expression in human bone marrow stromal cells. *Blood* 95:3094-3101, 2000.
Tablin et al., Membrane phase transition of intact human platelets: correlation with cold-induced activation. *J Cell Physiol.* August; 168(2):305-13, 1996.
Tetsuro-Takahiro Fujimoto et al., Production of functional platelets by differentiated embryonic stem (ES) cells in vitro. *Blood* 102: 4044-4051, 2003.
Thon et al., Platelet Storage Lesion: A New Understanding From a Proteomic Perspective. *Transfusion Medicine Reviews;* 22(4): 268-279, 2008.
Tomizuka et al., Hypersensitivity to thromboxane A2 in cholesterol-rich human platelets. *Thromb Haemost;* 64(4):594-9, 1990.
Yip et al., "Primary platelet adhesion receptors". IUBMB Life (*International Union of Biochemistry and Molecular Biology: Life*) 57 (2): 103-8, 2005.
Yomtovian et al., A prospective microbiologic surveillance program to detect and prevent the transfusion of bacterially contaminated platelets. *Transfusion;* 33:902-909, 1993.
Zucker et al., Reversible alteration in platelet morphology produced by anticoagulants and by cold. *Blood* 28:524-534, 1954.

What is claimed is:

1. A method for preserving platelets, comprising:
   (a) admixing cells with a cell media comprising a polyethylene glycol having an average molecular weight of from 200 g/mol to 500 g/mol less in a concentration of from about 0.1% (wt/v) to about 4% (wt/v);
   (b) wherein the method comprises storing the cell media comprising the platelets at a temperature of from about 0.1° C. to about 25° C.

2. The method of claim 1, wherein the concentration of the polyethylene glycol is from about 1% to about 3%.

3. The method of claim 1, wherein the concentration of the polyethylene glycol is from about 1.1% to about 2.5%.

4. The method of claim 1, wherein the cells are platelets, and wherein the method allows for storage of the platelets for more than 5 days without irreversible aggregation of the platelets.

5. The method of claim 4, wherein the method allows for storage of the platelets for at least 5-30 days without irreversible aggregation.

6. The method of claim 1, wherein the temperature is from about 0.1-10° C.

7. The method of claim 6, wherein the temperature is from about 0.1-5° C.

8. The method of claim 1, wherein the polyethylene glycol is PEG-200, PEG-225, PEG-250, PEG-275, PEG-300, PEG-325, PEG-350, PEG-375, PEG-400, PEG-425, PEG-450, PEG-475, or PEG-500.

9. The method of claim 8, wherein the cell media does not contain or only contains trace amounts of ethylene glycol, diethylene glycol, and/or triethylene glycol.

10. The method of claim 1, wherein the cells are platelets, and wherein the cell media comprises or consists of Acid Citrate Dextrose (ACD) solution, the polyethylene glycol, and the platelets.

11. The method of claim 1, wherein the media does not contain or only contains trace amounts of ethylene glycol, diethylene glycol, and/or triethylene glycol.

12. The method of claim 1, wherein the media further comprises about 0.3-3% of a compound having the structure:

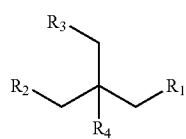

(II)

wherein:

$R_1$, $R_2$, and $R_3$ are each independently hydrogen, a polyethylene glycol comprising 1-5 repeating units, or a polypropylene glycol comprising 1-5 repeating units; and $R_4$ is hydrogen, alkyl$_{(C1-12)}$, substituted alkyl$_{(C1-12)}$, or a —(CH$_2$)$_x$—R$_5$; wherein:

x is 0, 1, 2, or 3; and $R_5$ is a polyethylene glycol comprising 1-5 repeating units or a polypropylene glycol comprising 1-5 repeating units.

13. The method of claim 12, wherein the compound is glycerol propoxylate, trimethylolpropane ethoxylate, pentaerythritol propoxylate, or pentaerythritol ethoxylate.

14. The method of claim 12, wherein the compound is pentaerythritol propoxylate.

15. The method of claim 1, wherein the cell media is comprised in an oxygen permeable polymer or plastic bag or container.

16. The method of claim 1, wherein the method comprises storing the cell media comprising the platelets at a temperature of from about 0.1° C. to about 15° C.

17. The method of claim 1, wherein the method comprises storing the cell media comprising the platelets at a temperature of from about 20° C. to about 25° C.

18. The method of claim 8, wherein the polyethylene glycol is PEG-375, PEG-400, PEG-425, or PEG-450.

19. The method of claim 1, wherein the polyethylene glycol has an average molecular weight of 200 g/mol to 420 g/mol.

20. The method of claim 1, wherein the polyethylene glycol has an average molecular weight of 300 g/mol to 450 g/mol.

* * * * *